US011000703B2

(12) United States Patent
Krishnaswamy et al.

(10) Patent No.: US 11,000,703 B2
(45) Date of Patent: May 11, 2021

(54) IMAGING SYSTEM AND METHODS OF HIGH RESOLUTION CHERENKOV DOSE IMAGES UTILIZING RADIO-OPTICAL TRIGGERING

(71) Applicants: THE TRUSTEES OF DARTMOUTH COLLEGE, Hanover, NH (US); DOSEOPTICS, LLC, Lebanon, NH (US)

(72) Inventors: Venkataramanan Krishnaswamy, Lebanon, NH (US); Petr Bruza, Lebanon, NH (US); Michael Jermyn, Lebanon, NH (US); Brian W. Pogue, Hanover, NH (US)

(73) Assignees: THE TRUSTEES OF DARTMOUTH COLLEGE, Hanover, NH (US); DOSEOPTICS, LLC, Lebanon, NH (US)

( * ) Notice: Subject to any disclaimer, the term of this patent is extended or adjusted under 35 U.S.C. 154(b) by 0 days.

(21) Appl. No.: 16/932,757

(22) Filed: Jul. 18, 2020

(65) Prior Publication Data
US 2020/0346041 A1 Nov. 5, 2020

Related U.S. Application Data

(63) Continuation of application No. PCT/US2019/014242, filed on Jan. 18, 2019.
(Continued)

(51) Int. Cl.
*A61N 5/10* (2006.01)
*G01T 1/20* (2006.01)
*G01T 1/22* (2006.01)

(52) U.S. Cl.
CPC ........ *A61N 5/1071* (2013.01); *A61N 5/1045* (2013.01); *A61N 5/1049* (2013.01);
(Continued)

(58) Field of Classification Search
None
See application file for complete search history.

(56) References Cited

U.S. PATENT DOCUMENTS

| 7,453,987 B1 | 11/2008 | Richardson | |
| 2011/0163236 A1* | 7/2011 | Arodzero | G01N 23/04 250/361 R |

(Continued)

OTHER PUBLICATIONS

International Patent Application No. PCT/US2019/014242, International Search Report and Written Opinion dated Apr. 24, 2019, 9 pgs.

*Primary Examiner* — Hoon K Song
(74) *Attorney, Agent, or Firm* — Lathrop GPM LLP

(57) ABSTRACT

A Cherenkov-based imaging system uses a radio-optical triggering unit (RTU) that detects scattered radiation in a fast-response scintillator to detect pulses of radiation to permit capture of Cherenkov-light images during pulses of radiation and background images at times when pulses of radiation are not present without need for electrical interface to the accelerator that provides the pulses of radiation. The Cherenkov images are corrected by background subtraction and used for purposes including optimization of treatment, commissioning, routine quality auditing, R&D, and manufacture. The radio-optical triggering unit employs high-speed, highly sensitive radio-optical sensing to generate a digital timing signal which is synchronous with the treatment beam for use in triggering Cherenkov radiation detection.

20 Claims, 14 Drawing Sheets

Related U.S. Application Data

(60) Provisional application No. 62/618,765, filed on Jan. 18, 2018.

(52) U.S. Cl.
CPC .......... *A61N 5/1081* (2013.01); *G01T 1/2002* (2013.01); *G01T 1/22* (2013.01); *A61N 2005/1054* (2013.01); *A61N 2005/1059* (2013.01)

(56) References Cited

U.S. PATENT DOCUMENTS

| | | |
|---|---|---|
| 2013/0259339 A1 | 10/2013 | Tian et al. |
| 2014/0224994 A1 | 8/2014 | Speller |
| 2015/0338545 A1 | 11/2015 | Arodzero et al. |
| 2016/0263402 A1* | 9/2016 | Zhang .................. A61N 5/1071 |

* cited by examiner

IMAGING SYSTEM AND METHODS OF HIGH RESOLUTION CHERENKOV DOSE IMAGES UTILIZING RADIO-OPTICAL TRIGGERING

CLAIM TO PRIORITY

The present application is a continuation of International Patent Application No. PCT/US2019/014242, filed Jan. 18, 2019, which claims priority to U.S. Provisional Patent Application No. 62/618,765, filed Jan. 18, 2018, the entire contents of which are incorporated herein for disclosure by reference.

GOVERNMENT SUPPORT

This invention was made with government support under grant numbers NIH 2R44CA199681-02 and NIH 1R44CA199836-01 awarded by National Institutes of Health. The government has certain rights in the invention.

INCORPORATION BY REFERENCE

The entire contents of all patents, published patent applications and other references cited herein are hereby expressly incorporated herein in their entireties by reference. In particular, the entire contents of PCT Patent Application Serial No. PCT/US14/66668 filed Nov. 20, 2014; PCT Patent Application Serial No. PCT/US12/38609 filed May 18, 2012; United States Patent Application US 2014/0114150, and U.S. Provisional Patent Application No. 62/153,417, filed on Apr. 27, 2015, and entitled "CHERENKOV IMAGING SYSTEMS AND METHODS FOR DETERMINING RADIATION DOSE," the disclosures of which are hereby incorporated herein in their entirety by reference.

BACKGROUND

High-energy particle or photon beams are used in treatment of many cancers. Such beams are typically provided by a linear accelerator (LINAC), or related apparatus. When treating cancers with radiation it is desirable to target the beam in time and space such that there is a high net ratio of energy deposited in the tumor relative to energy deposited in normal tissues outside the tumor, resulting in a high therapeutic ratio of tumor to normal tissue dose.

When treating patients with a high-energy radiation beam it is desirable to verify that the beam shape is as planned. Additionally, when beams enter tissue it is important to accurately predict how radiation beam shape varies with depth in tissue, to ensure adequate dosage to tumor tissue while minimizing dosage to surrounding normal tissues. If beam shape and orientation are adjusted, such as by positioning deflection magnets or shielding devices, it is important to confirm the resulting beam shape and dosage profile are as desired. Radiation treatment centers may therefore desire to confirm beam shape and dose profile for each patient or as part of routine calibration and maintenance. Moreover, aiming, shaping, timing, and other characteristics of therapeutic radiation beams should be verified during routine quality assurance or quality audit and recalibration prior to the administration of treatment to patients, where inadvertent exposure of non-tumor tissue to radiation must be minimized.

In fact, manufacturers of radiation treatment devices routinely document beam shapes and dosage profiles produced by common configurations of their devices for training and guiding operators in using their machines. Further, they must seek regulatory approvals of their machines, and, as part of the regulatory approvals process, must provide documentation of beam shapes and dosage profiles achievable by their machines. Manufacturers therefore also need to accurately verify and document beam profiles for this regulatory approval process.

Cherenkov light emitted by tissue or by media with radiological properties similar to those of tissue (such as water) can be used as a proxy for radiation delivered to tissue and to other media, its real-time use for beam construction has been elusive with current technology. Cherenkov light has been used for qualitative applications, in systems that detect Cherenkov radiation emitted by tissue and other media in real-world clinical settings, however, these systems required direct interfacing to the LINAC.

Current Cherenkov imaging camera systems require interfacing with LINAC timing signals to support Cherenkov imaging synchronized to during beam pulses and background imaging with beam off. Such synchronized operation with the LINAC allows imaging optically weak Cherenkov light emissions in well-lit rooms. Although these synchronization signals are accessible through standard LINAC service panels, electrical interfaces must be carefully designed to make sure there is no interference with normal LINAC operations, and access to these signals requires rigorous verification and validation requirements on interfacing electronics, as well as approvals from LINAC vendors and regulatory authorities.

SUMMARY

Accordingly, the present system is a Cherenkov-based imaging system using a remote, beam sensing, radio-optical triggering unit (RTU) which does not require an electrical interface to the LINAC. The RTU provides trigger signals for Cherenkov and background imaging. The radio-optical triggering unit, as well as related systems and methods, leverages scattered radiation present in the room during radiation treatment with high-speed, highly sensitive radio-optical sensing to generate a digital timing signal synchronous with the treatment beam for use in triggering Cherenkov radiation cameras.

The system and method provides for rapid and economic characterization of complex radiation treatment plans prior to patient exposure, utilizing a radio-optical triggering unit (RTU). Further, the system and method provide for economically imaging Cherenkov radiation emitted by tissue and other media in real-world clinical settings, such as settings illuminated by visible light, utilizing the RTU.

BRIEF DESCRIPTION OF THE DRAWINGS

In the drawings, like reference characters generally refer to the same parts throughout the different views. It is to be understood that the invention is not limited in its application to the details of construction and to the arrangements of the components set forth in the following description or illustrated in the drawings. The invention is capable of other embodiments and of being practiced and carried out in various ways. The drawings are not to scale, emphasis instead being placed upon illustrating certain principles of the system and method. In the following description, various embodiments are described with reference to the following drawings.

DETAILED DESCRIPTION

Figure 1A:
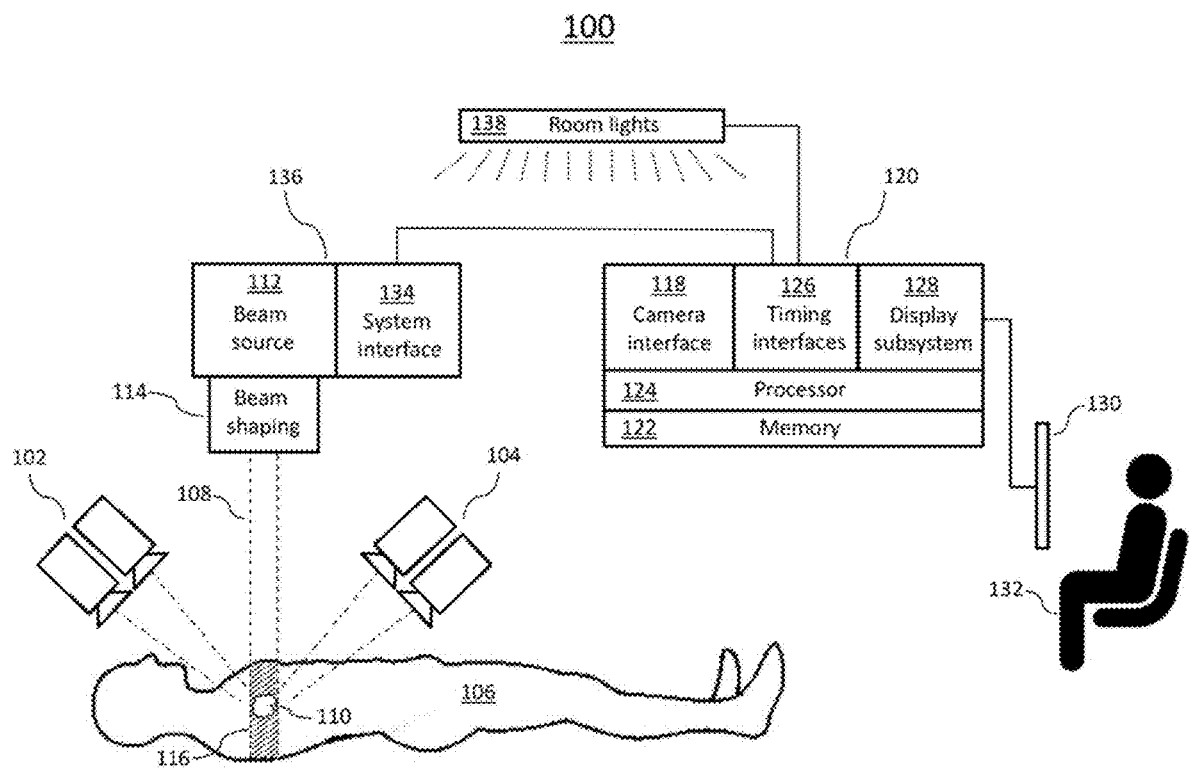
FIG. 1A schematically depicts an illustrative system for performing monitored radiotherapy with time-controlled room lighting and camera sensing of light emissions from a subject.

The present system is directed to advanced Cherenkov-based imaging systems, tools, and methods of feedback control and quantification in high resolution radiation dose images utilizing a remote, beam sensing triggering solution which does not require an electrical interface to the LINAC. In accordance with certain embodiments, systems and methods are disclosed that enable:

(1) rapid and thorough optimization, quality auditing, commissioning, and characterization of beams from LINACs and other systems producing external-therapy radiation, (2) rapid and economic characterization of complex radiation treatment plans prior to patient exposure, and (3) economical detection of Cherenkov radiation emitted by tissue and other media such as water in settings illuminated by visible light using a beam sensing triggering solution.

Charged particles (e.g., electrons, positrons, protons, alpha particles) moving faster than the speed of light in a dielectric medium decelerate while emitting photons. These photons are termed Cherenkov (a.k.a. "Cerenkov" and similar spellings) radiation. In particular, charged particles moving with sufficient speed cause Cherenkov radiation emission in human tissue or water. Cherenkov radiation can also result from irradiation by high-energy photons used in cancer therapy (e.g., 6-18 MV), because Compton scatter of these photons produce secondary electron emission having sufficient kinetic energy to produce Cherenkov radiation in the medium. Cherenkov emission in human tissue has been detected with incident radiation in the range of 6 to 24 MeV energies for electrons and x-ray photons. Although no particle of nonzero mass can move at or above the speed of light in vacuum (velocity c), it is common that particle velocities can exceed the speed of light v in a material media, v being less than c, when excited to kinetic energies greater than a few hundred kiloelectron volts (keV). Since Cherenkov emission depends on particle velocity, more-massive particles (e.g., protons, alpha particles) need correspondingly higher energies in order to produce Cherenkov radiation in a given medium, and so Cherenkov is only emitted from larger-mass charged particles such as protons at considerably higher kinetic energy than required for electrons.

Cherenkov radiation (or "Cherenkov light") is emitted at an acute angle θ to the path of a particle moving at velocity $v_p$, where $\cos θ = c/(nv_p)$ and n is the refractive index of the medium; when numerous charged particles move at suitable velocity in a collimated beam, a Cherenkov glow is emitted in a conic pattern at angle θ to the beam, which is approximately 41 degrees from the direction of travel. Cherenkov emission has a continuous spectrum across the entire ultraviolet, visible, and near-infrared spectrum with intensity varying as the inverse square of the wavelength (up to a cutoff frequency). Thus, Cherenkov emission at higher frequencies (shorter wavelengths) is more intense, giving rise to Cherenkov light's characteristic blue color when viewed by eye or camera.

When Cherenkov light is induced locally inside water or tissue, it is predominantly blue in color, but with a broad spectrum which tapers off into the green, red, and near-infrared (NIR) with an inverse square wavelength dependence given by the Frank-Tamm formula. This light when emitted within tissue is attenuated by absorbers significantly reducing the blue green wavelengths and largely just leaving the red and NIR wavelengths for transmission over a few millimeters. This light in the tissue can also excite other molecular species within the tissue to induce photo-luminescence (i.e., fluorescence or phosphorescence).

Cherenkov light is of significance for medical radiation systems because its intensity at any given point in a volume of tissue, as captured by imaging equipment, correlates with the intensity at that point of radiation that meets the criteria for inducing Cherenkov light. Cherenkov light emission is thus a proxy for high-energy radiation intensity. Therefore, Cherenkov light enables quantitative and relative observation of a high-energy radiation beam by an imaging device (e.g., camera) not aligned directly with the beam and thus not subject to damage by it.

Accordingly, we describe systems, tools, and methods for using Cherenkov light emission from an intersection of a radiation beam from a standard linear accelerator with a subject or phantom, including emission of fluorescent light from fluorophores stimulated by Cherenkov light, to localize and quantify the radiation beam. In certain embodiments, operative feedback including Cherenkov imaging, e.g., of a phantom (nonliving test object), is employed to enable a human operator or computational system to adjust a therapeutic radiation machine or plan of treatment for purposes of design, commissioning, quality auditing, adjustment, treatment plan verification, or the like in real-time. In certain other embodiments, localized high-accuracy measurements of therapeutic radiation flux by an additionally available measurement device such as an external portal imaging device, ionization chamber, or diode, are integrated with Cherenkov imaging to produce Cherenkov visualizations of dose delivery calibrated to accurate dose units. In some embodiments, high resolution dose images are provided in tomographic or otherwise enhanced characterizations of therapeutic radiation beam profiles.

The Cherenkov-based imaging systems, tools, and related methods are described with reference to the following definitions that, for convenience, are set forth below:

I. Definitions

As used herein, the term "a," "an," "the" and similar terms used herein are to be construed to cover both the singular and plural unless otherwise indicated herein or clearly contradicted by the context.

The term "camera" herein describes an electronic camera capable of imaging Cherenkov radiation and/or radiation emitted by fluorescent substances (fluorophores) excited by Cherenkov radiation.

The term "interface" is used herein to describe a shared boundary across which two separate components of a system exchange information, which can be between software, computer hardware, peripheral devices, humans and combinations of these. Moreover, the operation of two separate components across the boundary, as in the interaction of the camera interface which is designed to interface with the camera, is referred to herein as "interfacing." In certain embodiments, the interfacing may be bi-directional. In other embodiments, the interfacing may be uni-directional. In specific embodiments, the term "interface" may reference a user interface such as a graphic user display and keyboard.

The term "high-energy radiation" is used herein to describe radiation that, considering the mass of particles involved, contains enough energy to generate Cherenkov radiation upon entry into a given medium with a given refractive index. As such, the use of the language "high-energy radiation" herein takes into account both the delivered particle and the medium irradiated.

The term "isocenter" herein references a point in space relative to the treatment machine which indicates the center of the treatment volume, e.g., in a system where various components of the system rotate, the isocenter is the point about which the components rotate. Location of the isocenter plays an important role in treatment planning, since ideally the isocenter should be centered in the target volume such as centered in a tumor; thus, patient positioning with respect to the isocenter is a significant factor for successful irradiation of cancerous tissue and consequently for treatment outcome.

The language "machine-readable medium" describes a medium capable of storing data in a format readable by a machine. Examples of machine-readable media include magnetic media such as magnetic disks, cards, tapes, and drums, punched cards and paper tapes, optical disks, barcodes, magnetic ink characters, and solid state devices such as flash-based thumbdrives, solid-state disks, etc. In a particular embodiment, the machine-readable medium is a network server disk or disk array. In specific embodiments, the machine-readable medium occupies more than one network server disks.

The term "subject" as used herein is to describe the object being irradiated with radiation, such as a phantom or human tissue.

The term "user" or "operator" are used interchangeably to describe any person that operates the systems of the present system by interfacing with a user interface.

II. Advancements in Cherenkov-Based Imaging Systems

Cherenkov-based imaging systems offer instantaneous radiation surface imaging of a subject exposed with high-energy radiation, in order to qualitatively record and verify accuracy of treatment at the time of exposure. Such systems generally include at least one camera capable of imaging Cherenkov light, an image processor, and a machine-readable medium designed to record and store the information; capture of the Cherenkov light from the subject is typically triggered by a signal tapped directly from a LINAC used to provide pulsed radiation to the subject.

The advanced Cherenkov-based imaging systems herein described use a radio-optical triggering unit (RTU) instead of a signal tapped directly from a LINAC and provide enhanced system features that afford the systems to more actively use this information through:
(1) feedback presentation of this information to control the radiation beam source;
(2) quantification of dose based on Cherenkov imaging, providing high resolution images; and
(3) improved dynamic range image capture through use of the beam sensing triggering solution described herein.

As such, one embodiment provides an advanced Cherenkov-based imaging system including:
    a radiation beam source (e.g., a particle accelerator or other device for providing high-energy radiation, which, for example, may be cross-sectionally shaped by a beam-shaping apparatus, e.g., a multi-leaf collimator), the radiation beam source may be a LINAC, LINACs typically provide a charged-particle beam, such as an electron or proton beam, with pulse duration between 3 and 6 microseconds with repetition rate of 60 to 360 pulses per second, inclusive;
    at least one camera capable of imaging Cherenkov radiation (and/or radiation emitted by fluorescent substances (fluorophores) excited by Cherenkov radiation); and
    one or more processing units that enables the control of the radiation beam source,
    wherein the Cherenkov radiation is detected by the camera after exposure of a subject to high-energy radiation from the radiation beam source. In certain embodiments, systems have desirable properties such as rapidity, three- and four-dimensionality, and water equivalence.

In certain embodiments, the systems include an illumination system adapted to substantially reduce interference with wavelengths of interest by using an LED illumination system.

Figure 1B:
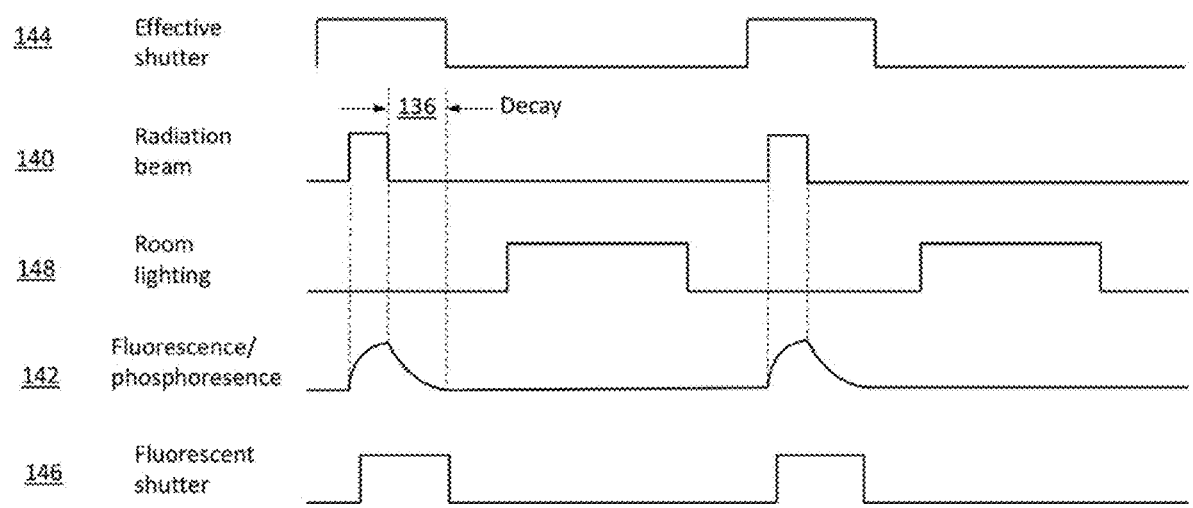
FIG. 1B is a diagram showing the approximate relationships of room lighting, beam pulses, light emissions, and camera shutter windows in the system of FIG. 1A.
Figure 2:
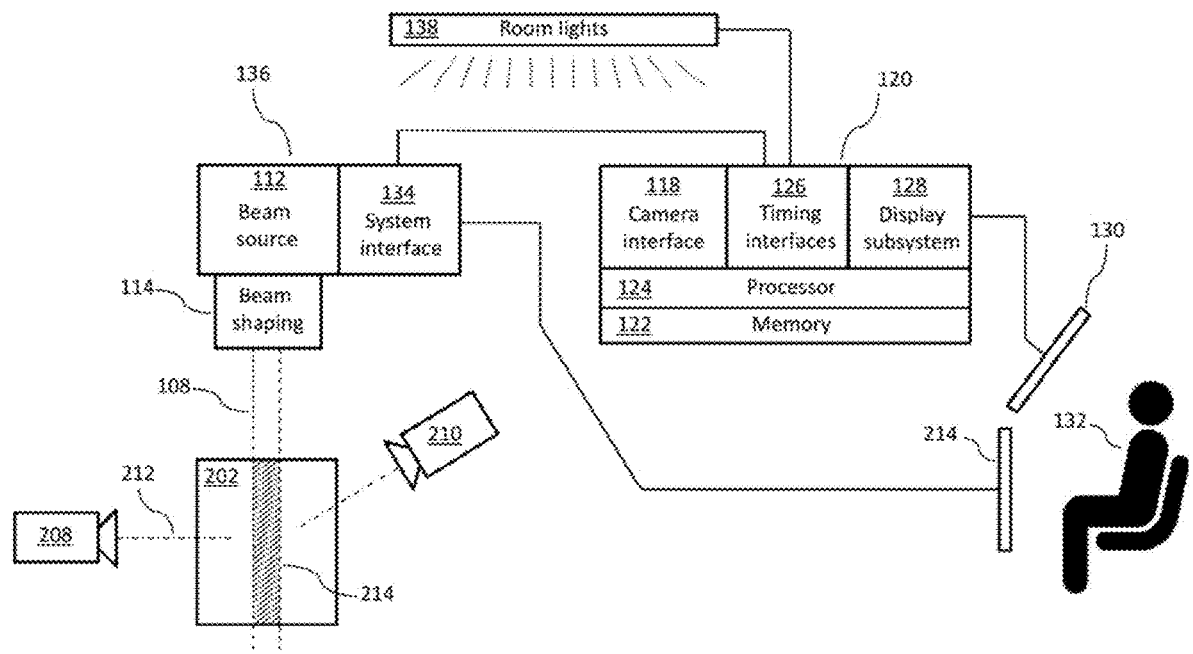
FIG. 2 is a schematic block diagram of an apparatus for coordinated direct feedback observation and adjustment/control of high-energy beam profiles in a therapeutic radiation system while imaging the beam depositing dose in a phantom.

FIG. 1A, FIG. 1B, and FIG. 2, described further herein below, depict certain aspects of systems that are relevant to various embodiments.

FIG. 1A schematically depicts portions of an illustrative external-beam radiation therapy system 100 similar to a system described in U.S. Provisional Patent Application No. 62/153,417. System 100 provides context relevant to various embodiments described herein. In particular, system 100 depicts high-sensitivity electronic cameras or groups of cameras 102, 104 used to image Cherenkov light and/or light emitted by fluorescent substances (fluorophores) excited by Cherenkov light and to localize locations on or in a human subject 106 from where this light is emitted. In certain embodiments, the subject 106 is preferably located within an environment from which light from uncontrolled sources, such as the sun and incandescent lamps, is excluded or minimized. In certain embodiments of the system 100 depicted in FIG. 1A, the subject 106 is placed in the path of a radiation beam 108 so that the beam 108 irradiates a tumor 110. Beam 108 is provided by a radiation beam source 112, e.g., a particle accelerator or other device for providing high-energy radiation, and typically is cross-sectionally shaped by a beam-shaping apparatus 114, e.g., a multi-leaf collimator.

In the illustrative system 100 of FIG. 1A, the source 112 is an accelerator that provides a beam 108 of electrons having energy of between 6 million electron volts (6 MeV) and 24 MeV, such as is used to deliver treatment energy to deep tumors as opposed to treatment of surface skin. Various other therapeutic systems could produce, for example, a photon beam of 6 MeV or higher or a high-energy proton beam. In general, various embodiments are combined with therapeutic radiation systems that produce beams capable of inducing Cherenkov radiation emission in human tissue, including but not limited to systems described explicitly herein.

In certain embodiments similar to system 100, cameras 102, 106 image the subject 106 from fewer or more points of view than are depicted in FIG. 1A, or non-stereoscopic cameras are used, or a single camera is arranged to move to more than one position with respect to the subject, or the subject 106 is supported in a manner that permits their rotation with respect to one or more cameras, or some combination of one or more of these or other imaging arrangements is employed. Cherenkov and/or fluorescent radiation emission occurs where the tissues (or tissue equivalent) of the subject 106 are irradiated by the beam 108, a volume herein termed the emission volume 116. Fluorescent light emissions can be induced by Cherenkov-light excitation of fluorophores in tissue, where such fluorophores are present, and are radiated isotropically rather than directionally as is the case with Cherenkov radiation.

In certain embodiments, the cameras 102, 104 are aimed to image at least part of the emission volume 116 and are coupled to a camera interface 118 of an image-processing system 120. Camera connections to the camera interface 118 may be wired or wireless and are not depicted in FIG. 1A for clarity. Herein, in certain embodiments, camera connections may serve both to transfer image data from a camera to the camera interface 118 and to convey commands (e.g., for setting shutter timing, exposure) from the camera interface 118 to the camera. In certain embodiments similar to system 100, light-modifying components such as filters and light intensifiers are aligned with cameras, or included in cameras, to intensify and/or selectively admit Cherenkov and/or fluorescence light; however, such light-modifying devices are omitted from FIG. 1A for simplicity. The camera interface 118 captures and stores digital images from the cameras 102, 104 in memory 122 for later retrieval and processing by at least one processor 124 of the image processing system 120. The processor 124 can exchange information not only with the camera interface 118 and memory 122 but with a timing interface 126, a display subsystem 128, and potentially other devices as well. The display subsystem 128 communicates with a user interface 130 through which a user 132 can interact with the imaging-processing system 120. In certain embodiments, timing interface 126 is adapted to communicate with a system interface 134 of the radiation therapy device 136 to determine timing of pulses of radiation from the source 112 and to control pulsed room lighting 138 to mitigate interference from room lighting during imaging of Cherenkov emissions and/or fluorescence by synchronizing lighting with image capture by cameras 102, 104, as discussed below with reference to FIG. 1B.

In certain embodiments of the system 100 of FIG. 1A, the imaging system cameras 102, 104 are spectrally-sensitive cameras capable of providing spectral data permitting distinction between Cherenkov and fluorescent light. Emitted Cherenkov and fluorescent light is subject to attenuation by absorbance as it propagates through and emitted by tissue, and in some embodiments spectrally-sensitive cameras permit distinction between light absorbed by oxyhemoglobin and by deoxyhemoglobin.

In certain embodiments of the systems, for example in the system 100 of FIG. 1A, raw or de-noised images from the imaging system are recorded in one or more suitable digital memory systems (e.g., memory 122) as documentation of the radiation treatment.

In certain embodiments, prior to each session for which monitoring of radiation delivery is desired, an enhancing and indicating agent is administered to the patient. In a particular example, the enhancing and indicating agent is a dose in the range of 20 milligrams per kilogram body weight of 5-delta-aminoievulinic acid (5-ALA), administered for an incubation time of approximately four hours before each divided radiotherapy session begins. In specific embodiments with a metabolically active tumor 110, some of the 5-ALA is metabolized to protoporphyrin IX (PpIX), which fluoresces when illuminated by Cherenkov light. PpIX production in normal tissue and tumor 110 is generally understood to be proportional to metabolic processes in those tissues; thus, a metabolically active tumor will tend to contain more PpIX and fluoresce more brightly. Other enhancing agents may be developed or utilized with the system described herein.

In particular, the system and method provide simple, accurate, quick, robust, real-time, water-equivalent characterization of beams from LINACs and other systems producing external-therapy radiation utilizing a radio-optical triggering unit (RTU) for purposes including optimization, commissioning, routine quality auditing, R&D, and manufacture.

The radio-optical triggering unit, as well as related systems and methods, leverages the scattered radiation present in the room during the treatment and employs high-speed, highly sensitive radio-optical sensing to generate a digital timing signal which is synchronous with the treatment beam for use in triggering Cherenkov radiation detection and does not rely on any electrical signal from the LINAC itself.

A. Radio-Optical Triggering Unit (RTU)

As such, one embodiment provides a radio-optical triggering unit (RTU) that performs a method including steps of:

detection of scattered radiation by a fast response time scintillator (SCI) coupled with a high speed, single-photon sensitive silicon photomultiplier module (SiPM) to detect exposure of a subject to high-energy radiation from a radiation beam source, in a particular embodiment the fast response time scintillator is an array of eight, 5-centimeter cubes of Bismuth Geranium Oxide (BGO);

the SCI performs conversion and amplification of the scattered radiation into optical photons, while the SiPM generates an analog electrical signal;

processing the analog signal to a digital timing signal, e.g., a transistor-transistor logic signal, wherein the digital timing signal is synchronized with the radiation beam source; and communication of the digital timing signal to trigger the operation of at least one camera capable of imaging one or more signals, e.g., Cherenkov radiation or scintillation signals (e.g., from scintillation patches placed on the patient's body).

In an alternative embodiment, the RTU times pulses of the high-energy radiation to provide a timing signal of improved accuracy, to provide interpolated signals early in each interval between beam pulses when fluorescent emission is present, and to provide interpolated signals late in each interval between beam pulses when only background illumination is present.

In one embodiment, the timing signal generated by the RTU is used to perform synchronous imaging of Cherenkov radiation produced by the treatment beams in tissue or other synthetic materials, as detailed herein. In an alternative embodiment, the timing signal generated by the RTU is used to perform synchronous imaging of scintillation signals produced by the treatment beams in tissue or other synthetic materials in the same manner as imaging the Cherenkov signals.

Figure 6A:
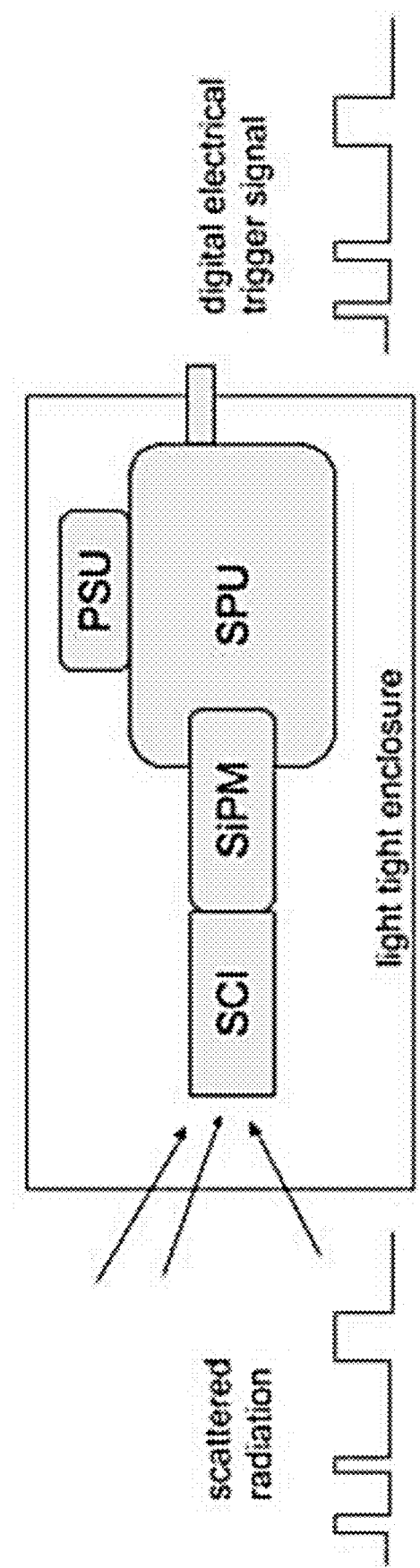
FIG. 6A shows a schematic of one embodiment of a radio-optical triggering unit, which uses a high speed, highly sensitive radio-optical sensing system to generate a digital timing signal synchronous with the treatment beam.

FIG. 6A shows a schematic of one embodiment of a radio-optical triggering unit, including a high speed, highly sensitive radio-optical sensing system to generate a digital timing signal synchronous with the treatment beam. The RTU has a fast response scintillation crystal SCI 602, such as a BGO (bismuth germanium oxide) crystal, that converts and amplifies scattered ionizing radiation into optical photons, which are detected by a high speed, single photon sensitive silicon photomultiplier module (SiPM), and the analog electrical signal generated by the SiPM is conditioned and converted to a digital (transistor-transistor logic) TTL signal by the signal processing unit (SPU) 608. In an alternative embodiment, an optional neutral density filter 604 is inserted between the scintillation crystal 602 and the SiPM 606 to control sensitivity.

In certain embodiments of the radio-optical triggering unit (RTU), the time signal is synchronized with the radiation beam source to trigger the operation of at least one camera capable of imaging Cherenkov radiation to detect Cherenkov radiation during beam pulses and imaging background images at times when beam pulses are not present. In particular embodiments, such synchronized operation with the LINAC allows imaging optically weak Cherenkov light emissions in well-lit rooms.

In certain embodiments of the radio-optical triggering unit (RTU), the step of communication is capable of instructing modification of additional downstream electronics and imaging system functions.

In certain embodiments of the radio-optical triggering unit (RTU), the rising edge of the timing signal is synchronous with the radiation beam source and is used to trigger the operation of at least one camera capable of imaging Cherenkov radiation. In certain embodiments, the rising edge of the timing signal is used for gating additional downstream electronics and imaging systems, e.g., such as the camera, e.g., C-Dose™ camera.

In certain embodiments of the radio-optical triggering unit (RTU), the fast response scintillator SCI is encapsulated in a light tight enclosure.

Figure 9:
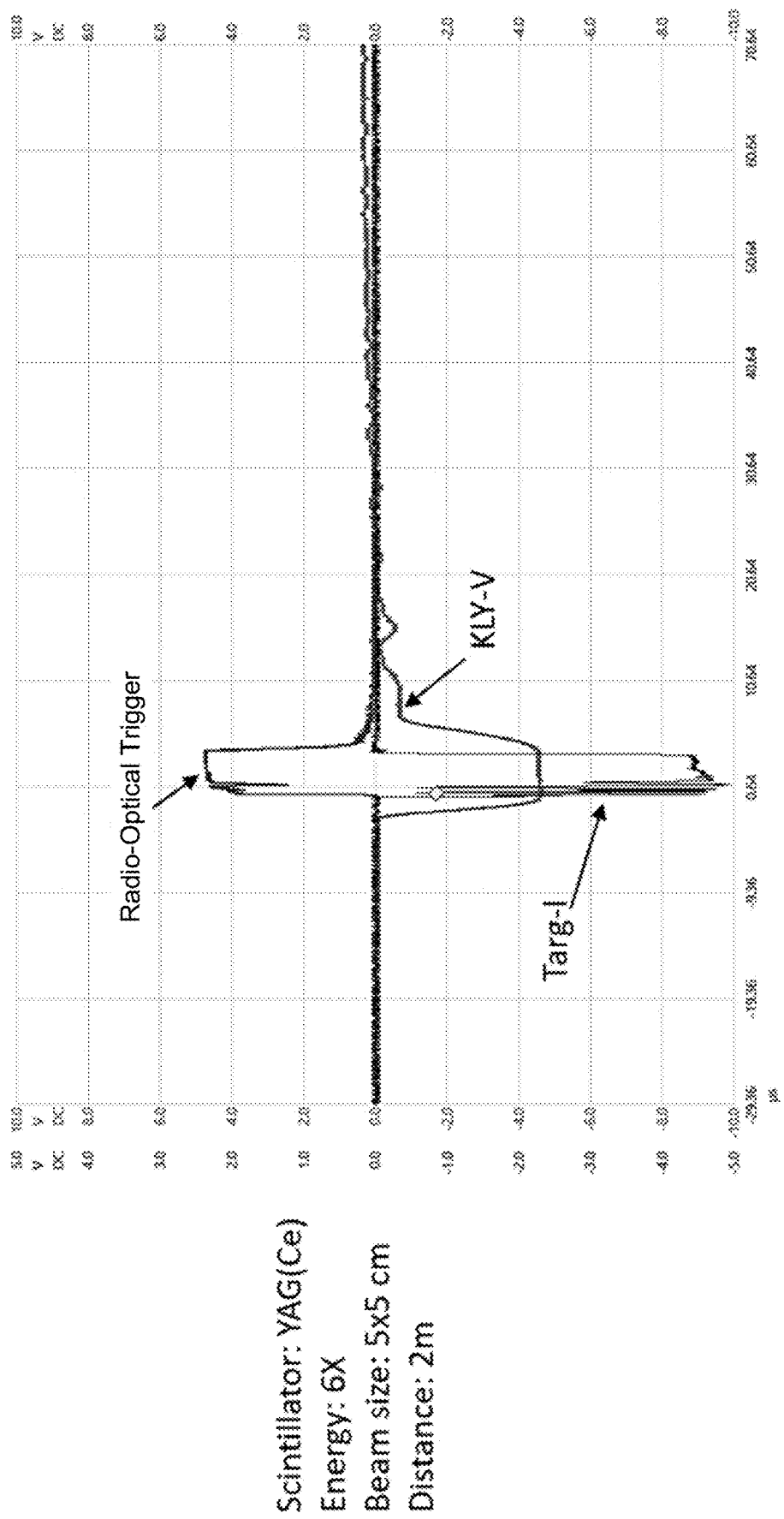
FIG. 9 is a graph that depicts an optical trigger signal matching both TARG-I and KLY-V signals.
Figure 10A:
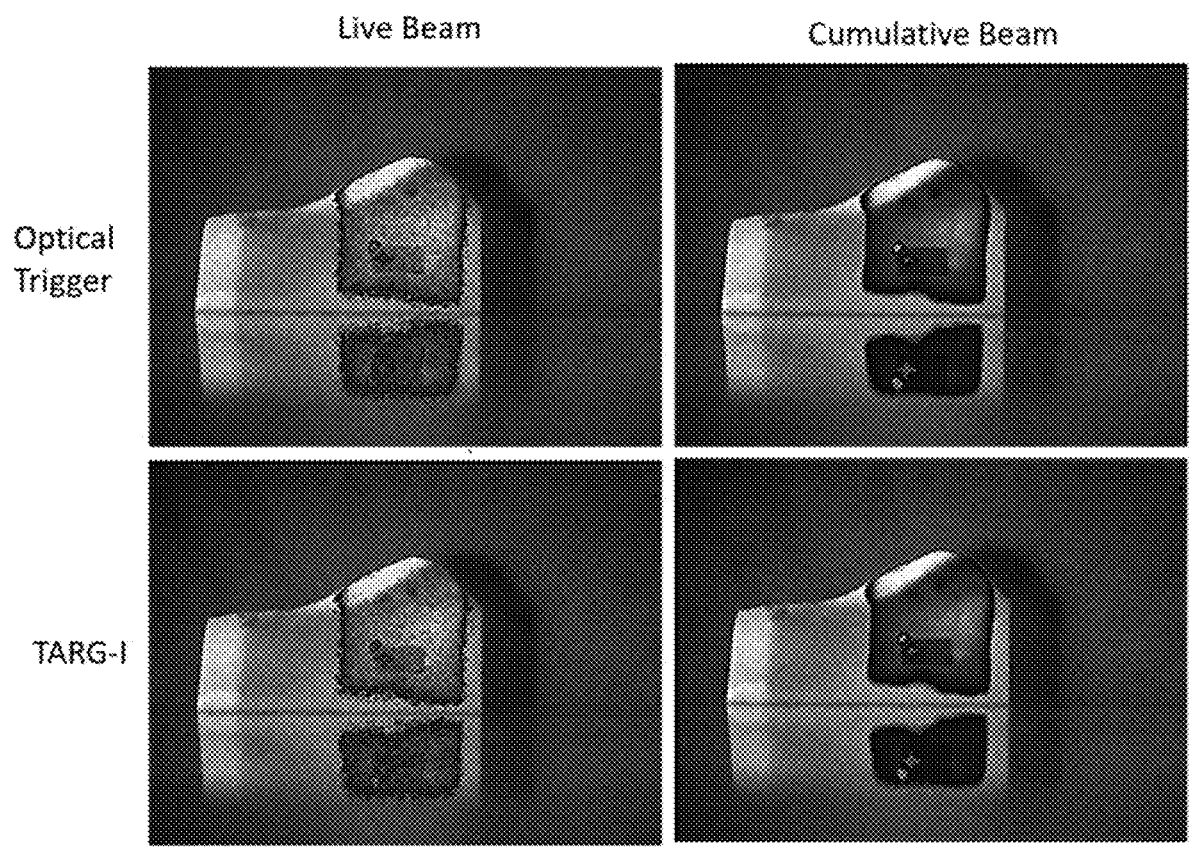
FIG. 10A provides multiple Cherenkov images indicating optical triggering matching TARG-I triggering.
Figure 10B:
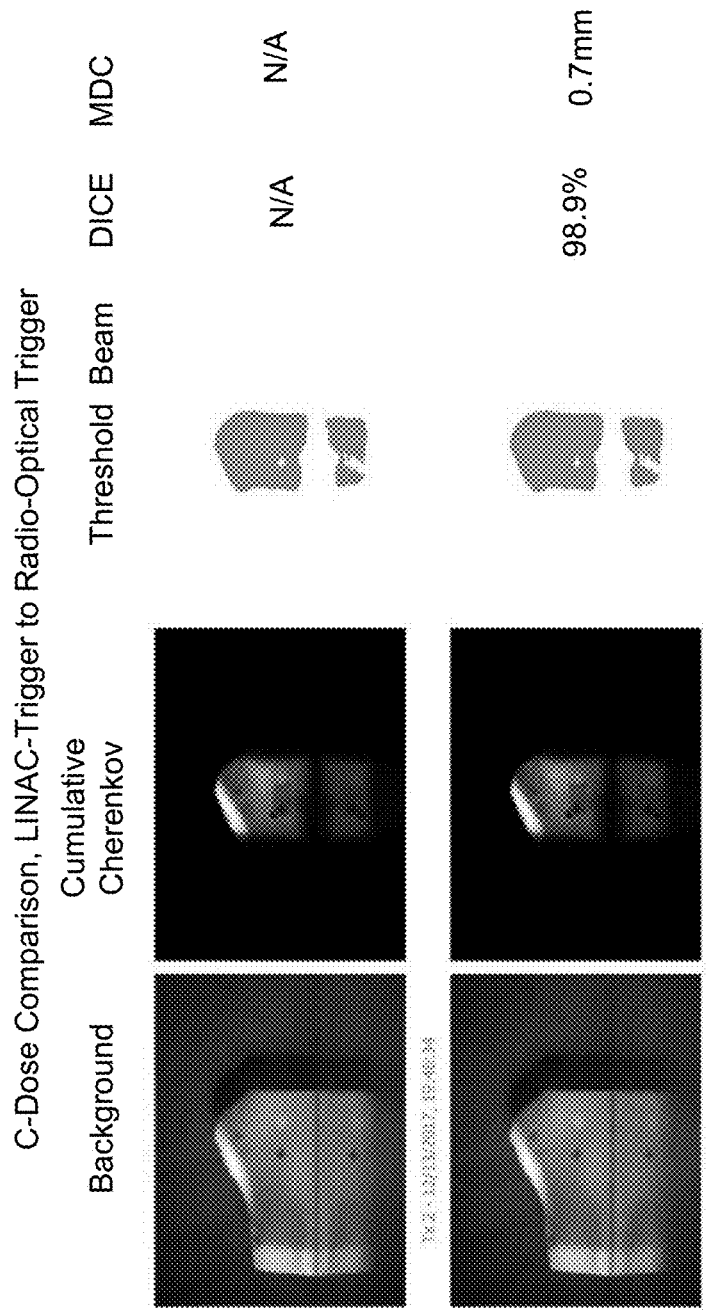
FIG. 10B provides multiple Cherenkov images and data indicating optical triggering matches the TARG-I triggering in location and intensity.

In certain embodiments, the signal from RTU fully substitutes for the LINAC supplied sync signals, such as TARG-I (typically used for imaging photon beams) or KLY-V (typically used for imaging electrons), which are typically used to synchronize the operation of prior cameras for imaging Cherenkov radiation with LINAC operation. In this respect, FIG. 9 depicts the optical trigger signals matching both TARG-I and KLY-V signals. Furthermore, FIG. 10A shows optical triggering matching the TARG-I triggering visually and 10B shows the optical triggering matches the TARG-I triggering in location and intensity.

In certain embodiments with the RTU, the system further comprises a communication tool with one or more processing units that enables the control of a radiation beam source.

In certain embodiments of the system, the system includes a radiation beam source. In certain embodiments, the radiation beam source is a particle accelerator, LINAC, or other device for providing high-energy radiation. In particular embodiments, the radiation beam source may be cross-sectionally shaped by a beam-shaping apparatus. In specific embodiments, the beam-shaping apparatus is a multi-leaf collimator.

Figure 6B:
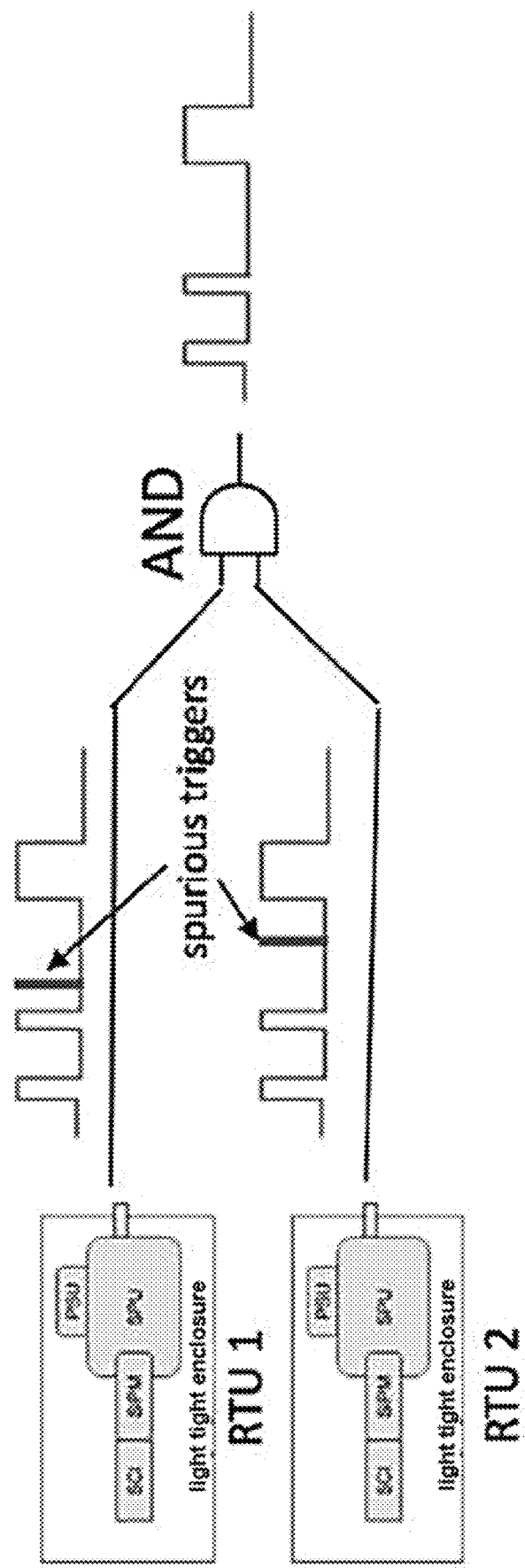
FIG. 6B is a schematic of two radio-optical triggering units with outputs AND-ed to suppress spurious triggers.

In certain embodiments of the advanced triggering systems, the system further comprises one or more additional radio-optical triggering units, multiple RTU modules being used to implement a co-incidence triggering mechanism. This design allows rejection of possible spurious triggering of the SCI, and coupled SiPM due to spontaneous emissions from the scintillator crystal or cosmic ray interactions. FIG. 6B below shows a schematic of this implementation employing two RTUs, where each of these modules are shown to be sensing a spurious trigger during the normal operational mode. In particular embodiments the outputs from two RTU modules are combined using a logical AND gate. Since spurious triggers occur randomly in time the AND gate effectively suppresses them at the output; but the radiation beam is sensed by both the RTUs and valid triggers synchronous with each other are passed to the cameras. In certain additional embodiments, the two RTUs are spatially separated, to reduce potential for spurious triggers.

Figure 7A:
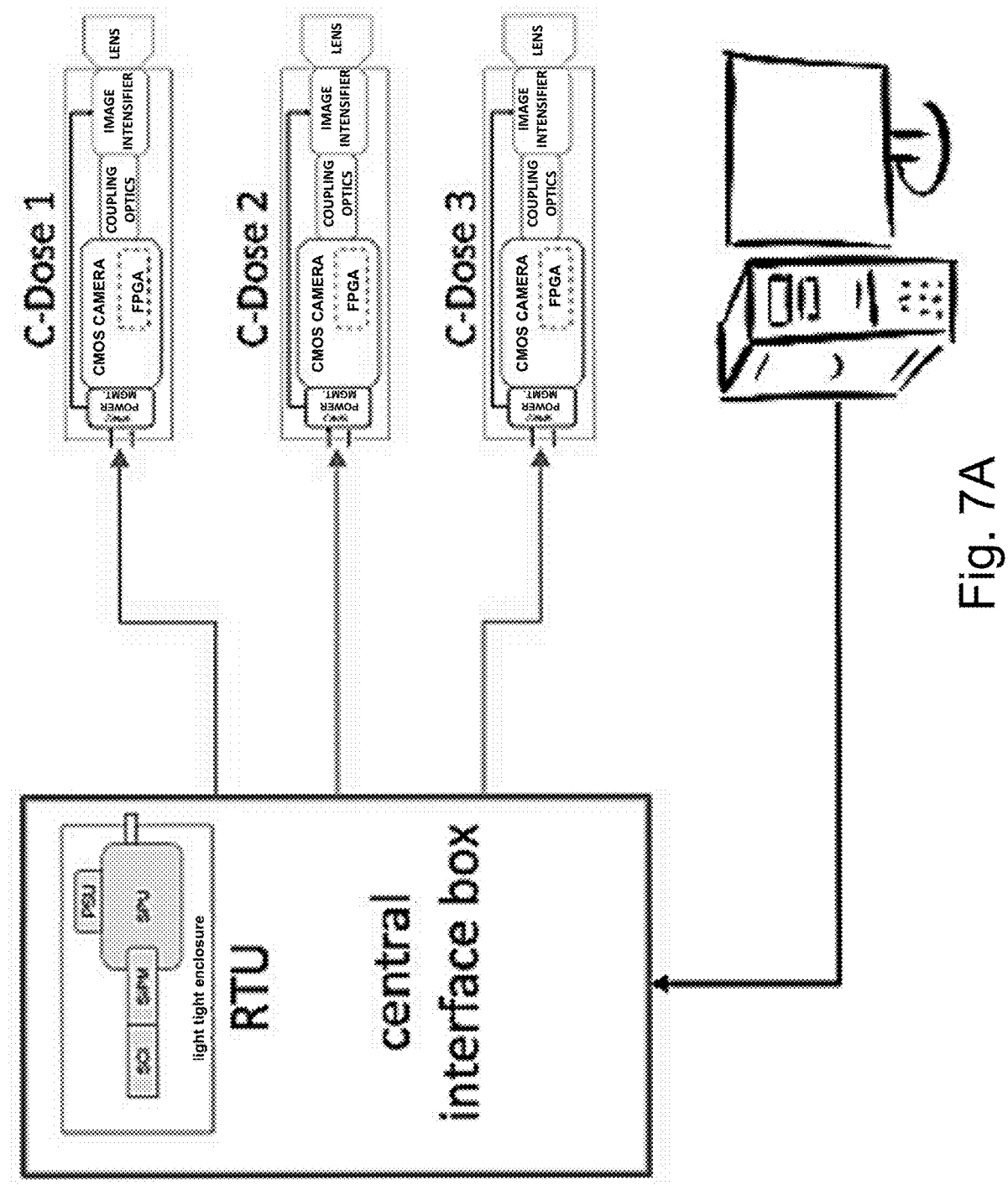
FIG. 7A is a schematic depicting one embodiment where the RTU placed within a central interface box, which distributes the synchronization signal to multiple connected cameras along with power.
Figure 7B:
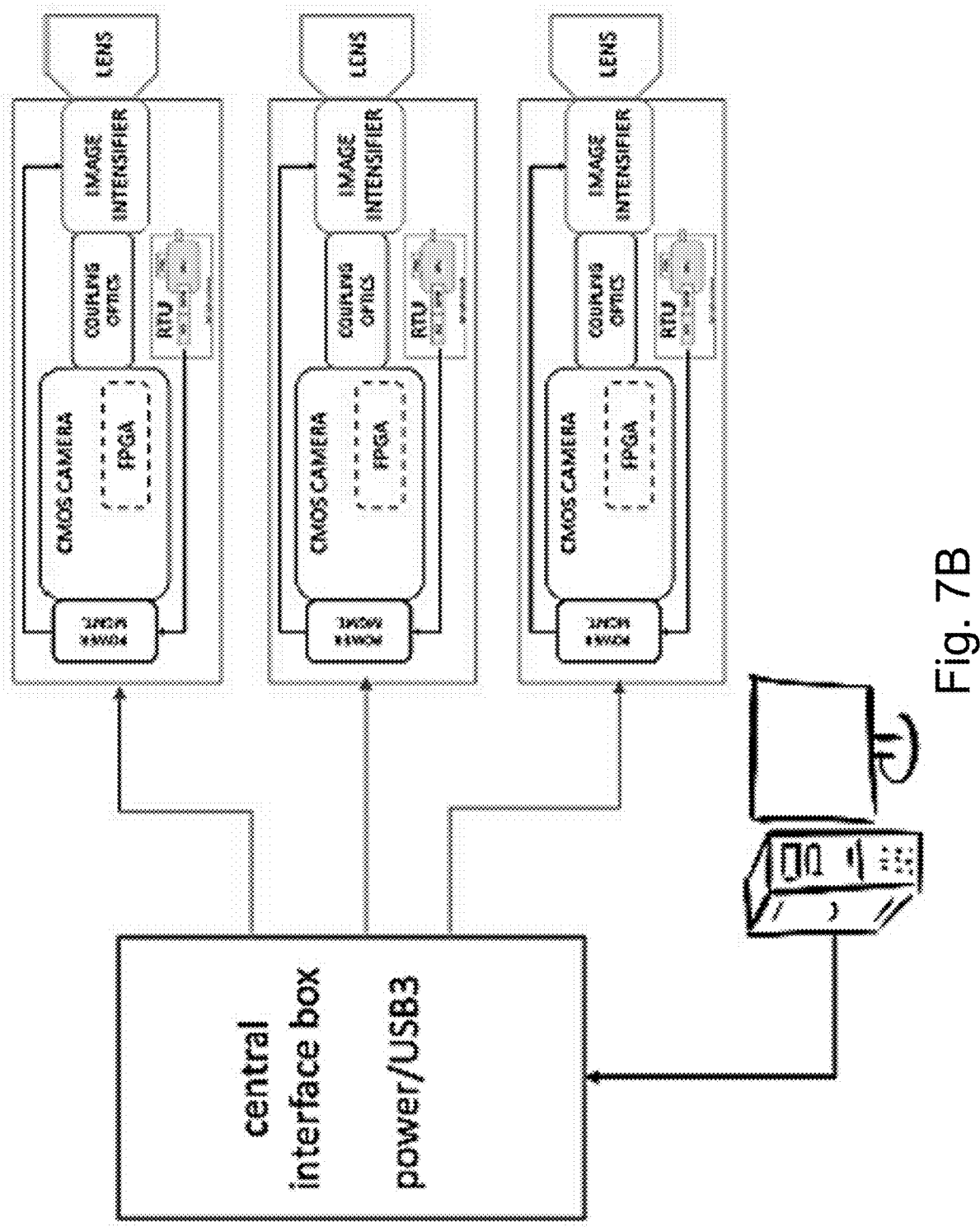
FIG. 7B is a schematic depicting one embodiment where the RTU is housed within a camera enclosure.
Figure 8:
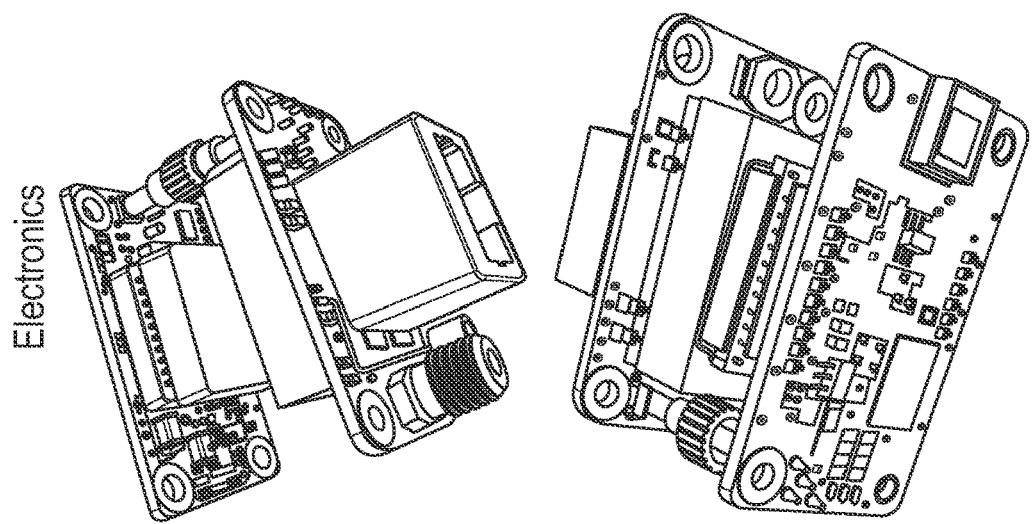
FIG. 8 is a representation of the case and components certain embodiments of the RTU.
Figure 8:
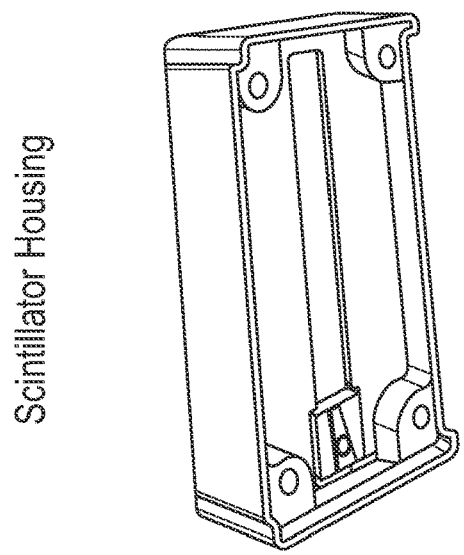
Figure 8:
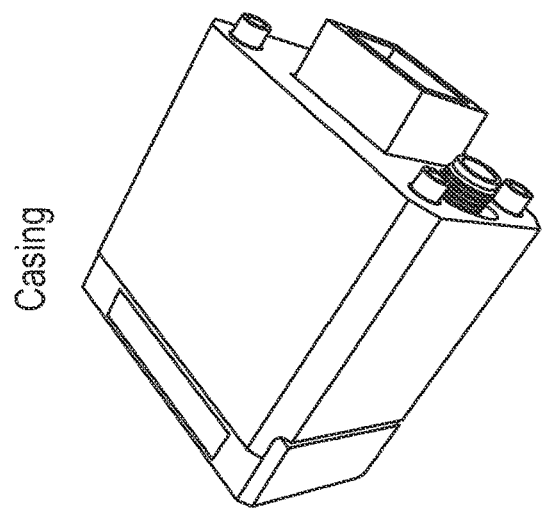

The RTUs may be compact and independent sensing modules, and as such, they may be configured in many different ways to improve redundancy, and support self-contained operation of Cherenkov imaging camera systems. Accordingly, and without intending to limit the system architecture including an RTU a system may include multiple RTUs, each RTU may be encompassed within camera units or may be separate from the camera. FIG. 7A shows one configuration where the RTU module is placed within a central interface box, which distributes the synchronization signal to multiple connected cameras along with the power. The RTU module in this depiction may be a basic unit or a coincidence triggering variant, which offers additional redundancy in the case of one of the RTU units failing. In an alternative embodiment, as shown in FIG. 7B, an RTU is housed within each camera enclosure. This configuration offers camera level redundancy and also enables simple single camera designs with built-in triggering capabilities.

In certain embodiments of the advanced triggering systems, the system further comprises an integrated power supply unit (PSU) 610 (FIG. 6A), that provides power to the radio-optical triggering unit including the SiPM 606 and SPU 608. In certain embodiments, at least the scintillation crystal 602 and silicon photomultiplier SiPM 606 are enclosed in a light-tight enclosure 612 to reduce interference from room lighting.

B. Direct Feedback Interface Control Units and Systems

In certain advanced Cherenkov-based imaging systems utilizing a radio-optical triggering unit (RTU), the system further provides direct feedback of the image information derived from capturing real-time Cherenkov radiation administration in order to instruct on the control of the beam source and/or beam shape. In certain embodiments, this is accomplished by means of incorporation of a direct feedback interface (DFI) control unit, wherein the DFI control unit is designed to provide direct/real-time communication between the camera and the radiation beam source unit and/or beam shaping unit (e.g., collimator), e.g., via a user display. Moreover, the Cherenkov-based feedback to the radiation beam source and/or beam shaping unit, may be used by developers or service people to optimize the radiation beam source and/or beam shaping unit.

As such, another embodiment provides a direct feedback interface (DFI) control unit including a processor configured by firmware to perform a method comprising:

detection of Cherenkov radiation (and/or radiation emitted by fluorescent substances (fluorophores) excited by Cherenkov radiation) after exposure of a subject to high-energy radiation from a radiation beam source;

creation of an image (e.g., image information);

comparative analysis of the image to a reference image; and communication of the results of the comparative analysis to the radiation beam source unit, wherein such communication is capable of instructing modification of the beam profile. In this way, the detected Cherenkov radiation may be used to directly control the linear accelerator, and the beam output. Another embodiment uses a radio-optical triggering unit (RTU) as herein described, further provides an advanced Cherenkov-based imaging system comprising a direct feedback interface (DFI) control unit. In certain embodiments, a direct feedback interface (DFI) control unit is incorporated into any system described herein. In certain embodiments, the system includes a Cherenkov-based imaging system including:

a radiation beam source which, for example, may produce a beam cross-sectionally shaped by a beam-shaping apparatus such as a multi-leaf collimator;

at least one camera capable of imaging Cherenkov radiation (and/or radiation emitted by fluorescent substances (fluorophores) excited by Cherenkov radiation);

one or more processing units that enable the control of the radiation beam source; and a direct feedback interface (DFI) control unit,
wherein the Cherenkov radiation is detected by the camera after exposure of a subject to high-energy radiation from the radiation beam source.

In certain embodiments, a beam profile based on detected Cherenkov light or Cherenkov-stimulated fluorescence is directly fed to the radiation beam source unit or a designer, operator, or maintainer who is testing therapeutic radiation machine design, commissioning a newly installed therapeutic radiation machine, or performing periodic quality auditing and/or adjustment of a therapeutic radiation machine, or who wishes for any other purpose (e.g., treatment-plan verification) to characterize the spatial and temporal delivery of radiation by a therapeutic radiation machine to a treatment volume. In certain embodiments, a LINAC machine delivering radiation in the form high-energy electrons is described as an illustrative therapeutic radiation system, but no restriction is intended by this usage; all other radiation systems capable of inducing Cherenkov radiation in tissue are contemplated and within the scope of the invention.

FIG. 2 is a schematic depiction of portions of an illustrative system 200 for the coordinated observation and adjustment of a device providing radiotherapy based on direct feedback control. In certain embodiments, system 200 is equipped with a subsystem interface for determining beam profiles and dynamics by observation and analysis of Cherenkov radiation. For example, in certain embodiments, a beam-calibration phantom 202 is placed in a zone where it is desired to measure a profile of a radiation beam 108 provided by a radiation treatment machine 136. In particular embodiments, the zone may be a volume above or beside a treatment table (not depicted). In certain embodiments, the phantom 202 is a fluid-filled tank, the fluid in the tank being a translucent or transparent fluid having an index of refraction greater than that of air; in a particular embodiment, the fluid is water. In certain embodiments portions of the walls of the phantom 202 are transparent to Cherenkov light, e.g., the top and sides of phantom 202 consist largely of glass or transparent plastic. In a particular embodiment, the phantom 202 has sides constructed of acrylic sheets; another particular embodiment has sides constructed of polycarbonate panels. In a specific embodiment, a small amount of scattering agent and/or fluorophore is added to the liquid in the phantom 202 to enhance scatter of Cherenkov light without significantly affecting propagation of the radiation beam 108, overcoming the inherent directionality of Cherenkov light from a collimated radiation beam and allowing more light to be detected laterally around the phantom 202. The system 200 may also include an apparatus for preventing interference by room lighting or may be blacked out to prevent interference of ambient light with measurements of the Cherenkov radiation. However, room blackout for relatively long periods (e.g., a multi-image acquisition interval) is in general more feasible with a phantom 202 rather than a patient because live subjects may find blackout disturbing (e.g., claustrophobic) and workers cannot observe a patient's condition during blackout, which raises safety concerns.

In an alternative embodiment, the tank is filled with a transparent fluid such as silicone oil. In yet another embodiment, the phantom is formed from a high-index, transparent, material, such as a cast high-index plastic, e.g., plastic water or solid water (e.g., anthropomorphic), and may have both fluorophores and light-scattering additives embedded within it.

In certain embodiments, the system 200 also includes one camera or a multiplicity of cameras; the illustrative embodiment of FIG. 2 includes two cameras 208, 210. For graphic simplicity the two cameras 208, 210 are depicted as being coplanar, but in certain embodiments, the cameras have lines of sight (e.g., line of sight 212 of camera 208) that are orthogonal to each other, e.g., in a plane that is orthogonal to the treatment beam 108. In certain embodiments, two orthogonal views suffice for the tomographic reconstruction of the three-dimensional light field intensity in the emission region 214 (cross-hatched region) from each simultaneously acquired pair of images from the cameras 208, 210. In particular embodiments, where only Cherenkov light is emitted from the emission region 214, the cameras 208, 210 may lie in a plane that is at angle $\theta$ with respect to the beam 108, where $\cos\theta = c/(nv_p)$, c being the velocity of light in a vacuum, n the index of refraction of the material filling the phantom 202 (assumed herein for illustrative purposes to be homogeneous, but not necessarily so), and $v_p$ being the velocity of particles in the beam 108. In various other embodiments, a single camera is arranged to move to more than one position with respect to the phantom 202, or the phantom 202 is supported in a manner that permits its rotation with respect to one or more cameras, or some combination of one or more of these or other imaging arrangements is employed to obtain sufficient information for beam profile characterization (e.g., tomography). In certain embodiments where the beam 108 is known to have a radially symmetric spatial profile), a single camera may be used to fully characterize the spatial profile of the beam 108. Also in other embodiments, the particle beam source 112 and beam shaping subsystem 114 are attached to a gantry that enables them to move about a phantom 202 or a patient in the irradiation zone, delivering radiation to and from a range of angles.

The cameras 208, 210 are aimed to image at least part of the emission volume 214 and are coupled to a camera interface 118 of an image-processing system 120. (Camera connections to the camera interface 118 may be wired or wireless and are not depicted in FIG. 2 for clarity.) In certain embodiments, the camera interface 118 captures and stores digital images from the cameras 102, 104 in memory 122 for processing by at least one processor 124 of an image processing system 120. The processor 124 is capable of exchanging information not only with the camera interface 118 and memory 122 but with a timing interface 126, a display subsystem 128, and potentially other devices. The display subsystem 128 communicates with a user interface 130 through which a user 132 can interact with the imaging-processing system 120. Timing interface 126 is adapted to communicate with a system interface 134 of the radiation therapy device 136 to determine timing of pulses of radiation from the source 112 and potentially to control pulsed room lighting 138 to avoid interference from room lighting during imaging of Cherenkov emissions and/or fluorescence by synchronizing lighting.

In certain embodiments, the phantom 202 is located within an environment that excludes significant amounts of daylight and light from other bright source such as room illuminators. In particular embodiments, the walls of the phantom 202 are coated on their interior surface with a light-absorbing coating except for camera viewing windows positioned in front of each camera, the coating being provided to absorb both stray light originating from outside the phantom 202 and to prevent emissions light from being reflected from the interior walls of the phantom 202 into a camera 208, 210.

In certain embodiments, a beam source 112 (e.g., particle accelerator or other device for providing high-energy radiation) is aimed to provide a beam 108 of radiation through beam-shaping apparatus 114 to phantom 202. In a particular embodiment, the source 112 provides a beam of electrons having energy of 6 million electron volts (6 MeV) or greater; in a particular embodiment, the beam energy lies between 6 and 24 MeV. In an alternative embodiment, the source 112 produces a photon beam of 6 MeV or greater. In another alternative embodiment, the source 112 provides a proton or heavy charged particle beam. In yet another alternative embodiment, the source 112 produces a beam of electrons or photons having a substantial percentage of electrons or photons having energy of 1 MeV or greater. In the illustrative embodiment of FIG. 2, the radiation therapy machine 136 is a LINAC providing a beam of 6 MEV electrons.

Reference is now made to FIG. 1B, which schematically depicts the timing relationships of certain embodiments of the system 100 of FIG. 1 according to some methods of operation. In signal diagrams given in FIG. 1B and elsewhere herein, timing relationships are not necessarily drawn to scale: e.g., the width of a pulse may be exaggerated relative to the delay between pulses, or the duration (width) of a pulse depicted for one signal may not be proportional to that depicted for another signal. With emphasis on the sequence of events, i.e., which signals are On and which are Off at any given moment, Cherenkov radiation is emitted during high-energy radiation beam pulses 140; timing and intensity of Cherenkov emission closely correlates to timing and intensity of radiation pulses 140. Cherenkov-stimulated secondary light 142 emitted from naturally occurring, artificially administered, or drug-metabolite fluorescent materials can lag the radiation beam 140 and can decay exponentially after each pulse of the beam turns off, as illustrated. The time of this decay depends upon the emission lifetime of the biochemical species that was excited.

In one illustrative mode of operation, an effective Cherenkov shutter interval 144 that includes beam pulse 140 is used to image light primarily emitted by Cherenkov mechanisms, and an effective fluorescent shutter interval 146 is used to capture light emitted from the human subject or phantom by fluorescent and/or phosphorescent mechanisms. In this exemplary arrangement and mode of operation, room lighting 148 is pulsed Off for the duration of Cherenkov light emission (i.e., for duration of radiation pulse 140) and fluorescent emission 142 so that the relatively weak optical signals of interest may not be swamped by ambient light: in effect, the optical signal to noise ratio is improved by turning room lighting 148 off during emissions imaging. If the period of such pulses is significantly shorter than the flicker perception threshold of human vision, some dimming of room lighting relative to an unpulsed mode of operation may be visible, but no irritating flicker would be observed. In another exemplary mode of operation, room light is not pulsed, but an intensification step of image acquisition (not depicted) is gated On only during Cherenkov light emission, thus effectively rejecting most of the ambient light. In an example, during Cherenkov and/or fluorescent light acquisition, light imaged by cameras 102, 104 in FIG. 1A is recorded as pairs of consecutive images, with a first image of each pair recording of Cherenkov light emitted during beam pulse 140 and a second image of each pair recording light emitted during the fluorescent shutter interval 146. In certain embodiments, processor 124 of FIG. 1A executes machine-readable instructions in associated memory, such as memory 122, to reconstruct first (Cherenkov) tomographic image sets of the subject from the first images of all image pairs captured, to reconstruct second (fluorescence) tomographic image sets of the subject from the second images of all image pairs captured, and to produce an image set of fluorophore distribution in the subject based upon some mathematical relationships (e.g., ratio) between the first and second tomographic image sets. In various other, similar systems and/or modes of operation, non-tomographic imaging is performed, optionally enhanced by signal-processing steps such as background subtraction and median filtering to remove saturated pixels.

In modes of operation such as those where 5-ALA is administered, the fluorophore distribution is related to metabolic activity in the subject, and the tomographic image set of fluorophore distribution in the subject is indicative of metabolic activity throughout the imaged volume of the subject. The processor 124, or a processor of another computer device (not depicted), can further execute machine-readable instructions in memory 122 to compare the tomographic image set of fluorophore distribution in the subject against a tomographic image set of fluorophore distribution in the subject obtained during a prior radiation treatment session in order to produce a tomographic image set indicative of treatment effectiveness, i.e., changes (if any) in tumor metabolic activity.

In certain embodiments of system 100 an enclosure (not depicted herein) surrounds the subject and excludes ambient light from the subject, supporting the imaging of faint Cherenkov and fluorescence emissions. Additionally or alternatively, the coordinated functioning of timing interfaces 126 of system 100 (FIG. 1A) and pulsed room lighting 148 (FIG. 1B) serve to mitigate or prevent interference of ambient lighting with measurement of Cherenkov light and fluorescent light from an emission volume in the subject. The term "apparatus for preventing interference by room lighting" as used herein shall mean either or both of an enclosure surrounding and excluding ambient light from the subject, and the combination of timing interfaces 126 and pulsed room lighting 148.

In certain embodiments, Cherenkov radiation and/or associated fluorescent emissions, which are proxies for radiation deposition by high-energy photons and charged particles, may be employed in spatial (i.e., one-dimensional, two-dimensional, or three-dimensional) and temporal beam characterization or profiling. Herein, "temporal beam profiling" refers to the characterization of variations in beam intensity over time, whether during single pulses or averaged over portions of pulses or whole pulses, and "spatial beam profiling" refers to characterization of the distribution of beam intensity across the two-dimensional beam cross-section, or as a function of depth in a phantom or living subject, or both. The fullest possible profile of a beam pulse, which is acquired in various embodiments, consists of a three-dimensional spatial profile re-acquired at time intervals sufficiently frequent to capture all temporal beam behavior of interest for a given purpose: in effect, such data constitute a three-dimensional movie of pulse intensity, herein termed a four-dimensional beam profile. Herein, unmodified reference to a "beam profile" may denote a one-, two-, three-, or four-dimensional beam profiles.

The illustrative embodiment of FIG. 2 includes a LINAC user interface 214 that is capable of exchange information with a user 132. In certain embodiments, the information thus exchanged may include settings of control parameters for beam shaping system 114, particle beam source 112, movements of a gantry (not depicted) for directing the beam 108, and other measurable and/or controllable aspects of the therapeutic machine 136, whose readings or behaviors may in general be made known to the user 132 and modified by the user 132. In certain embodiments, the user 132 may, in several examples, be a designer monitoring the performance of a LINAC machine under development, a technician performing commissioning of a newly installed LINAC system, a technician performing periodic or scheduled quality auditing and/or adjustment of the LINAC system, a technician validating the delivery of a patient treatment plan using a phantom 202 prior to administration of the plan to a living subject, or a person who wishes for any other purpose to study and possibly adjust the temporal, spatial, and other characteristics of a beam 108 produced by therapeutic radiation system 136 in various modes of operation, and the interactions of such a beam with a phantom 202 and possibly with additional phantoms, living subjects (e.g., animal or human), or other targets.

In certain embodiments, Cherenkov-based imaging enabled by the imaging subsystem 120 supports visual, qualitative, and relative quantification characterization of profiles (one, two, three, or four-dimensional) of the beam 108, including such aspects as translations and rotations of the beam 108, shaping of the beam 108 by various settings of the beam-shaping subsystem 114, changes in particle energy (Cherenkov spectra and emission angles are both functions of particle energy, making such properties detectable in principle by the imaging subsystem 120), alterations in beam intensity (detectable because for a given particle energy, beam intensity and Cherenkov light brightness are proportional), and other aspects. Unlike methods used in the prior art for the characterization of beam profiles, the Cherenkov-based system 200 of FIG. 2 and other embodiments can acquire two- or three-dimensional beam profiles at rates limited only by the optical and other technical characteristics of the cameras (e.g., cameras 208, 210) and associated equipment (shutters, intensifiers, etc.): Cherenkov light (and/or fluorescent emissions stimulated by Cherenkov light) is intrinsically a continuous, high-resolution, four-dimensional source of information about radiation flux in the irradiated volume 214. Four-dimensional characterization of individual beam pulses is possible in various embodiments. Such data can be processed by the processor 124—e.g., in a tomographic manner, or using various model-based and other imaging approaches that will be familiar to persons versed in the art of medical image processing—to reveal features of interest in one, two, three, and four dimensions (e.g., derivative images and comparative images, delivered-dose maps) that are not available from existing technologies. In further examples, temporal performance of the therapeutic machine 136 can be assessed within a single pulse, or between pulses, or during the warm-up phase of operation of the LINAC. This information can be used by the operator 132 to adjust the performance of system 134. For example, the user 132 can issue commands to alter beam shaping by the beam-shaping subsystem 114. In another example, the user 132 or another person may make mechanical or electrical adjustments to the beam-generating mechanism of the source 112. In certain embodiments, all adjustable aspects of the operation of system 136 can be adjusted in a manner informed by the Cherenkov-derived information collected and processed by the image-display subsystem 120. In certain embodiments, such information may be transmitted to other computing and memory devices (not depicted) for post-processing, long-term storage, studies comparing different therapeutic machines or configurations, simulation, and other purposes. Advantageously, certain embodiments enable the rapid, high-resolution, four-dimensional characterization of radiation delivery to the phantom 202, without need to reposition the cameras 208 210 or the phantom 202, as well as adjustments of therapeutic machine 136 in a manner informed by such detailed and timely characterization.

Moreover, certain embodiments enable efficient positioning of a phantom 202, or of other targets, with respect to the isocenter of the LINAC 136 (or other therapeutic radiation machine), in order that beam characterization or other tasks may be performed. In certain embodiments, the therapeutic radiation system indicates its isocenter location using intersecting visible lasers. In various embodiments, these lasers can be imaged by the same cameras (e.g., cameras 208 and 210) that are used to image Cherenkov and/or fluorescent light. Software control and feedback as described herein (e.g., through the system interface 134 and imaging subsystem 120) provide isocenter alignment information to the user 132. In a particular example, isocenter alignment laser images may be compared to physical or virtual registration marks on the phantom 202 as imaged to the user 132, and the phantom's position is adjusted accordingly: for example, control of platform positioning of the system 136 is conducted through the system interface 134, either manually by the user 132 or as determined by software computed by the imaging subsystem 120 or another computing device, to produce satisfactory alignment of isocenter of the phantom 202 or a region or target therein. Such embodiments minimize the time required for phantom setup and offer, for example, advantageous time savings for quality audit processes compared to lower-resolution electronic beam-locating systems. Because the camera or cameras of various embodiments have relatively very high spatial resolution and can be dual-used for both laser observation and Cherenkov observation, embodiments have a flexibility of set-up which exceeds that of known electronic diode or ionization chamber ionization processes.

In certain embodiments, the user interfaces 130 and 214 are supplemented or replaced by direct informatic communications interfaces and the human user 132 is supplemented or replaced by a computational system, such as a software program or artificial intelligence, that is configured to exchange information with image-processing subsystem 120, with the system interface of the therapeutic machine 136, and potentially with other measuring devices, mechanical systems, computing devices, and other devices or systems. In such embodiments, the software program or artificial intelligence performs some or all of the functions of evaluation, comparison, and adjustment that in the embodiment of FIG. 2 are performed by the human user 132.

Figure 3:
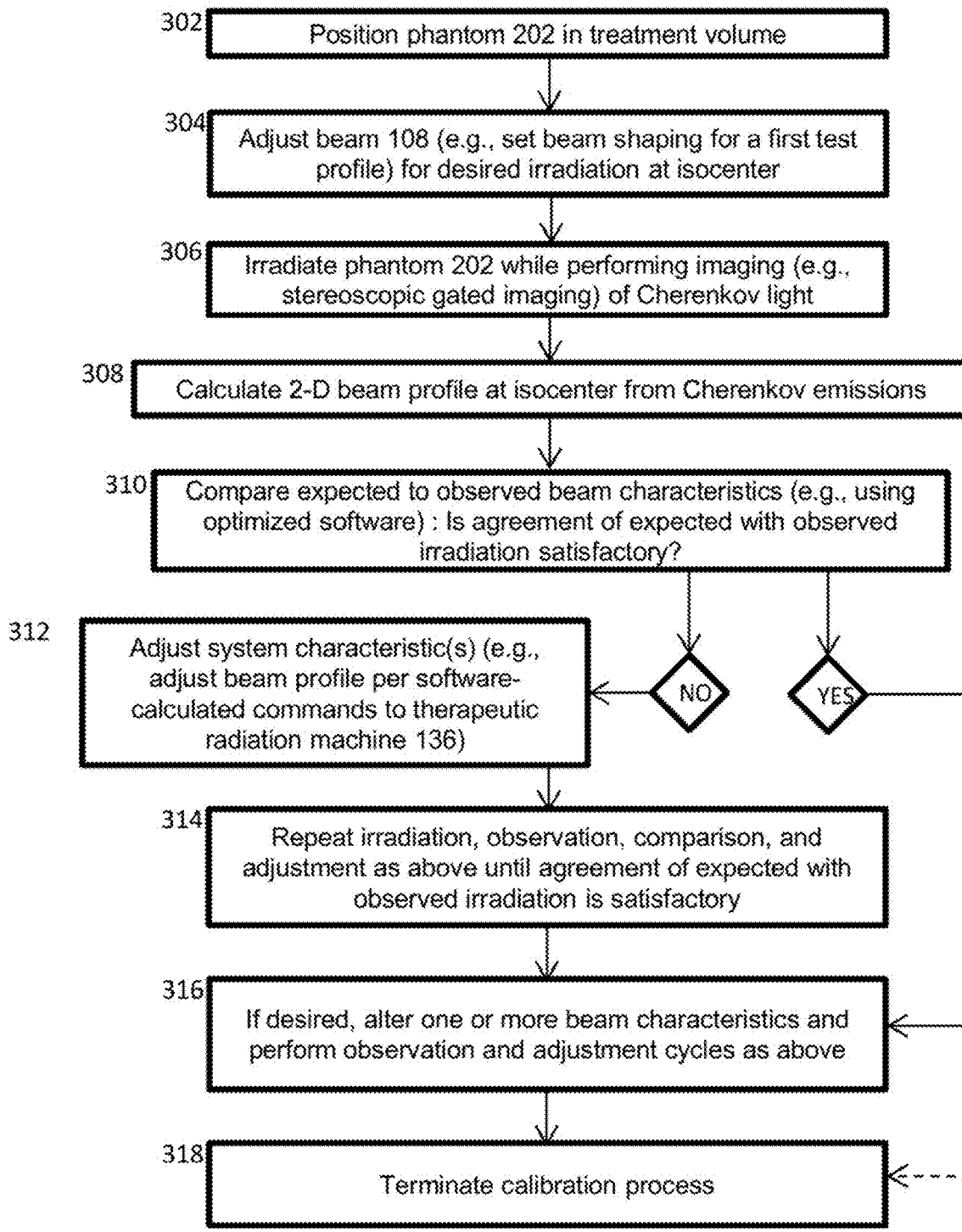
FIG. 3 is a flow chart of an illustrative method of operation of the system of FIG. 2.

In certain embodiments the operation of system is as illustrated by the flowchart of method 300 of FIG. 3, adjustment of the therapeutic system 136 is performed to produce a beam of desired characteristics within a specified accuracy range. In a preliminary positioning step 302 that may entail imaging of the system isocenter, the phantom 202 may be positioned within the treatment space of the system 136 so that the center of the phantom 202, or some other point within the phantom 202, is located at the system isocenter. In a beam-programming or adjustment step 304, the system 136 may be set to produce a beam 108 of a given character for irradiation of the phantom 202: such characteristics as intensity, pulse duration, pulse frequency, number of pulses, and two-dimensional beam profile as determined by the beam-shaping subsystem 114, among other characteristics, may be set to predetermined values. The predetermined values may be specified to serve a manufacturer's test plan, or as part of a patient treatment plan, or according to other criteria. In an irradiation step 306, one or more pulses of radiation are supplied by the therapeutic system 136, while imaging (e.g., stereoscopic gated imaging) of the Cherenkov light and/or secondary fluorescent light induced in the phantom by the radiation is performed. In an image-processing or beam-profile calculation step 308, data from the cameras 208, 210 is processed by the imaging subsystem 120 to produce, in this illustrative method, a two-dimensional irradiation pattern or beam profile at the system isocenter. In a display and comparison step 310, an expected profile and the observed profile are compared. Such comparison may be visual and ad hoc, or quantitative, or may combine several modes of comparison: in any case, such comparison produces a judgement, whether ad hoc or numerical, as to whether the expected irradiation pattern is sufficiently similar to the observed radiation pattern or not. If it is sufficiently similar, then the method may proceed to the testing 316 of another configuration of the system 136 or may terminate. If agreement between expected and observed radiation is unsatisfactory, then an adjustment step 312 is performed, in which one or more adjustable aspects of the mechanism and/or operation of the system 136 is performed by one or more of the operator 132, software, or an additional person. In a looping or convergence phase 314, irradiation and observation 306, beam profile calculation 308, comparison 310, and possibly adjustment 312, as described above, are repeated until satisfactory agreement between expected and observed radiation delivery is observed, a different system configuration is set up for testing 316, or the operator elects to end the procedure 318.

The calibration method 300 is illustrative of a broad class of procedures and methods by which the system 200 or various other embodiments may be operated. The systems and methods of most embodiments entail rapid and information-rich feedback to characteristics of the therapeutic system 136 based on observed and processed Cherenkov light or secondary fluorescence induced in the phantom 202 by the radiation beam 108.

C. Enhanced Beam Characterization: Integration of Cherenkov and Non-Cherenkov Sensing Another embodiment provides high resolution dose quantified Cherenkov-based images, through enhanced beam characterization. In particular, certain embodiments use a radio-optical triggering unit (RTU), further address the challenges of fast 3D dosimetry utilizing a technique that allows for real-time dose imaging, e.g., in water phantoms. While known non-Cherenkov radiation measurement devices, such as external portal imaging devices (EPID), can provide a 2D transverse distribution of a transmitted beam, and the Cherenkov imaging provides an accurate lateral view of the dose; the tools and methods described herein provide the integration of these measures by providing for the simultaneous acquisition of EPID images and lateral Cherenkov images. In certain embodiments, the integration of these measures produces a consistent 3D distribution of the deposited dose. In particular embodiments the non-Cherenkov radiation measurement device, e.g., EPID, and the Cherenkov techniques provide images with high frame rates (~10 fps) which permits real-time 3D beam reconstruction. As such, and in particular embodiments, this affords the ability to perform pre-treatment plan verification and quality assurance due to the high spatial and temporal resolution of the measured 3D dose distributions produced.

Traditionally, measurement methods for therapeutic radiation beams have depended on radiographic or Gafchromic film dosimetry for obtaining planar two-dimensional (2D) dose distributions inside a dosimetry phantom placed inside the treatment zone. Although film dosimetry is high-resolution, the process is cumbersome, not real-time, and may exhibit processing-dependent variability. Other known techniques include electronic portal imaging devices (EPIDs), ionization chamber arrays, and semiconductor arrays. For example, Theraview Technology's EPID images over a 40×40 cm square planar array with 1024×1024 pixels and 12-bit acquisition. A digital analogue to film dosimetry, EPID imaging is easy to use—EPIDs can be integrated with therapeutic systems and software-controlled—but the true experimental measurement may only be made at a single planar slice: thus, for EPIDs and other planar-type dosimetry methods, fully three-dimensional beam characterization is difficult and time-consuming to perform or may be impossible, while beam characterization in 3D over time (herein referred to as "four-dimensional" characterization) is extremely difficult and rarely, if ever, performed. Also, planar array-based systems have inherently limited resolution due to the finite spacing of the detectors.

Additional dosimetry methods currently under development include gel and plastic or liquid scintillation dosimetry. Despite several advantages, gel dosimetry is time consuming and requires post-processing and a readout mechanism such as optical computed tomography or magnetic resonance imaging, while scintillation methods require careful calibration and suppression of the stem effect. Finally, none of the currently known techniques are truly water equivalent, as the active medium is not water itself, which is of particular importance, as water is the gold-standard dosimetry medium due to its radiological close equivalence to tissue, cheap abundance, high purity, and ease of interinstitution standardization.

As such, another embodiment uses a radio-optical triggering unit (RTU), to provide a quantifier integration (QI) unit to perform a method comprising:

detection of Cherenkov radiation (and/or radiation emitted by fluorescent substances (fluorophores) excited by Cherenkov radiation) after exposure of a subject to high-energy radiation from a radiation beam source, and establishment of a Cherenkov radiation image;

detection of non-Cherenkov radiation after exposure of a subject to high-energy radiation from a radiation beam source, and establishment of a non-Cherenkov radiation measurement; and integration of the non-Cherenkov (i.e., quantitative) radiation measurements (e.g., from an ionization chamber or an EPID) with the Cherenkov radiation image (e.g., tomography), to produce a quantitatively calibrated high resolution Cherenkov image. The language "high resolution" as used herein describes high spatial and temporal resolution of the measured dose distribution, e.g., three-dimensional dose distribution. The quantitatively calibrated Cherenkov images represent beam geometry and intensity that are labeled with absolute dose units. These images may be used to establish a calibration where a given intensity of Cherenkov light at a given point of the phantom is experimentally associated with a particular intensity of ionization radiation in absolute dose units as measured by, for example, an EPID or ionization chamber. Further, in particular embodiments, non-Cherenkov radiation measurements (such as ionization chamber measurements) at sampling of discrete locations within the phantom or treatment volume (e.g., along the beam axis) can be used to produce a table or map (one-, two-, or three-dimensional) of local conversion factors that link units of observed Cherenkov brightness to absolute dose units in different portions of a beam.

In certain embodiments of the quantifier integration (QI) unit, the non-Cherenkov radiation measurement device is selected from the group consisting of an ionization chamber, EPID, diodes, and any combination thereof. In certain embodiments, the method may further comprise the step of communication of the quantitatively calibrated high resolution Cherenkov image to the radiation beam source unit. In this way, in certain embodiments, the detected Cherenkov radiation may be used to directly control the linear accelerator, and the beam output. In certain embodiments, the quantitatively calibrated high resolution Cherenkov image may be stored on a second a machine-readable medium (e.g., wherein the second machine-readable medium is the machine-readable medium of a DFI control unit). In certain embodiments, the non-Cherenkov radiation measurements allow quantitative estimation of the depth-vs.-dose curve from the Cherenkov radiation image.

Another embodiment provides an advanced Cherenkov-based imaging system utilizing a radio-optical triggering unit (RTU), including a quantifier integration unit. In certain embodiments, a quantifier integration (QI) unit may be incorporated into any system described herein. In certain embodiments, an advanced Cherenkov-based imaging system includes:

a radiation beam source (e.g., a particle accelerator or other device for providing high-energy radiation, which, for example, may be cross-sectionally shaped by a beam-shaping apparatus, e.g., a multi-leaf collimator);

at least one camera capable of imaging Cherenkov radiation (and/or radiation emitted by fluorescent substances (fluorophores) excited by Cherenkov radiation);

one or more processing units that enables the control of the radiation beam source;

a non-Cherenkov radiation measurement device; and a quantifier integration unit, wherein the Cherenkov radiation is detected by the camera and non-Cherenkov radiation is detected by the non-Cherenkov radiation measurement device after exposure of a subject to high-energy radiation from the radiation beam source.

Alternatively, in certain embodiments, the quantifier integration unit is implemented and integrated into an existing system via a supplemental kit, including for example, the quantifier integration unit and any component of the system described herein not present in the existing system to which the kit will be added.

Figure 4A:
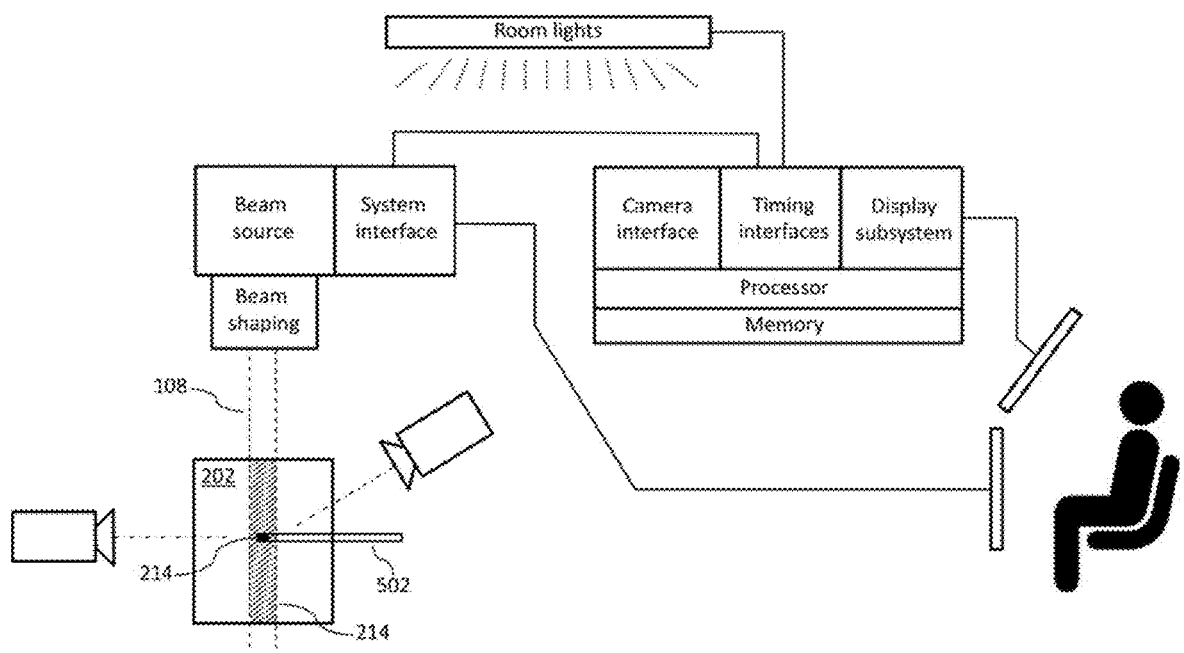
FIG. 4A is a schematic block diagram of an apparatus for the calibration of Cherenkov observations to in situ, high-accuracy radiation measurements in a therapeutic radiation system and phantom.

Reference is now made to FIG. 4A, which schematically depicts portions of an illustrative system 400 according to certain embodiments. System 400 resembles system 200 of FIG. 4A but with the addition of a non-Cherenkov radiation measurement device 502. In certain embodiments, the non-Cherenkov radiation measurement device is an ionization chamber. For example, a typical ionization chamber is a gas-filled chamber in which high-energy (ionizing) radiation creates free charges that can be detected and whose rate of appearance corresponds to the intensity of high-energy radiation within the ionization chamber. The term "ionization chamber" is often applied to denote entire radiation-probe systems that include an ionization chamber, not only to the chamber per se. Ionization chamber probes are generally considered the gold standard for calibration of therapeutic radiation systems because they give a precise and highly localized measure of the ionizing radiation delivered by a therapeutic system at a given point, e.g., a point within a water-filled phantom. In particular embodiments, the ionization chamber is the cylindrical, waterproof Farmer-type ion ionization chamber, which is recommended by various dosimetry protocols for dose measurement of radiotherapy beams. The chambers of such probes typically have volumes of 0.6-0.65 $cm^3$ and can report measured calibrated exposure accurate to National Institute of Standards & Technology (NIST) certified standards, which can be directly mapped to dose delivery at that point. The value of having one or more measures of exposure or dose allows calibration of the Cherenkov intensity into similar intensity units.

In certain embodiments, measurements from ionization chamber are combined/integrated with Cherenkov imaging (e.g., tomography) in order to produce accurately calibrated Cherenkov images or non-image measurements. In certain embodiments, a localized, highly precise measurement of radiation intensity is obtained by an ionization chamber at a given point (e.g., a point inside a water-filled phantom), the ionization chamber is removed, and the intensity of Cherenkov light emitted under identical radiation conditions by the sub-volume of the phantom corresponding to that previously occupied by the ionization chamber is observed. (This order of events may be varied; e.g., Cherenkov imaging may precede ionization chamber measurement.) A calibration is thus enabled by which a given intensity of Cherenkov light at a given point of the phantom is experimentally associated with a particular intensity of ionization radiation as measured by ionization chamber in absolute dose units. Ionization chamber measurements at sampling of discrete locations within the phantom or treatment volume (e.g., along the beam axis) can be used to produce a table or map (one-, two-, or three-dimensional) of local conversion factors that link units of observed Cherenkov brightness to absolute dose units in different portions of a beam. In an example, the resulting mapping of units is depth-dependent; in another example, the mapping is dependent on depth and on radial distance from beam center; in another example, the mapping is dependent on depth, radial distance from beam center, and distance from beam center. Thus, in certain embodiments, the tools and methods herein described enable the production of Cherenkov images of beam geometry and intensity that are labeled with absolute dose units, not merely with units of optical brightness.

In certain embodiments, for example in the illustrative system 400 of FIG. 4A, the non-Cherenkov radiation detection device 402 is a Farmer-type ionization probe inserted into the liquid-filled phantom 202. The actual gas chamber 404 of the probe 402 is at one tip of the probe 402. In particular embodiments, the volume of the chamber 404 is presumed to be sufficiently small relative to the irradiated volume 214 to permit meaningfully localized characterization of beam 108 intensity.

Figure 4B:
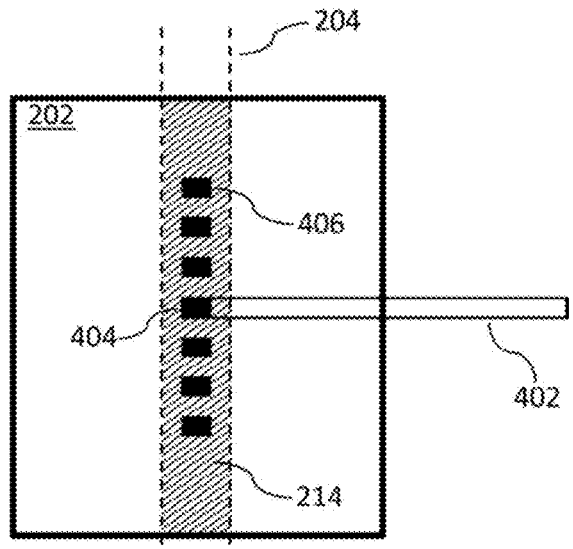
FIG. 4B is a more detailed view of portions of the system of FIG. 4A.

FIG. 4B depicts a closer view of one embodiment of the phantom 202 and probe 402, omitting cameras and other apparatus for clarity. In one illustrative method of operation of the system 400, the probe 402 may be moved so that the ion chamber 404 occupies a series of positions along the axis of the beam 108. In FIG. 4B, these points (e.g., position 406) are depicted as evenly spaced along a line and seven in number, but in general need not be evenly spaced and may be of any number or spatial arrangement. In certain methods of operation, either the entire phantom 202 may be moved along the axis of the beam 108 or the location of the chamber 404 may be moved. For clarity, only positions of the chamber 404, not the whole probe 402, are depicted in FIG. 4B.

In certain embodiments, and in the illustrative method partly illustrated in FIG. 4B, ionization chamber measurements of radiation intensity are made centrally along the axis of beam 108. In certain embodiments, after all measurements, the probe 402 is removed from the phantom 202 and one or more Cherenkov images (i.e., images of Cherenkov light or secondarily emitted fluorescent light) of the irradiation volume 214 are acquired. The average intensity of the observed light from within each of the seven measurement volumes is then directly correlated with radiation intensity as measured by ionization chamber. In one example, a continuous one-dimensional calibrative function can be calculated (e.g., by interpolation) from the discretely measured correspondences of radiation intensity to light intensity and applied to subsequent Cherenkov images of the phantom in order to accurately associate radiation intensity units with light-intensity units. In certain other methods of operation, radiation intensity measurements may be made within the irradiation volume 214 according to various geometric schemes other than or addition to that depicted in FIG. 4B (e.g., measurements may be located so as to sample a planar cross-section, or more than one planar cross-section, or a given sub-volume of the irradiation volume 214, or multiple one-dimensional transects similar to that depicted in FIG. 4B).

Certain embodiments advantageously combine the features of ionization chambers or other high-precision radiation tools with those of Cherenkov imaging. Ionization chamber dose measurements are highly accurate but slow and typically not acquired in more than one dimension (e.g., along beam axis for depth versus dose curves, or orthogonally to beam axis for beam profile measurements) at a time. In comparison, Cherenkov imaging has the inherent strengths of rapidity and provision of two-, three-, and four-dimensional data very quickly. Cherenkov imaging does, however, require calibration for quantitative accuracy of dose estimation. Using the tools and methods described herein, combining the two types of measurements—i.e., high-accuracy point or small-volume dose measurements and Cherenkov imaging—allows exploiting the strengths of both modalities while mitigating their weaknesses.

Figure 5:
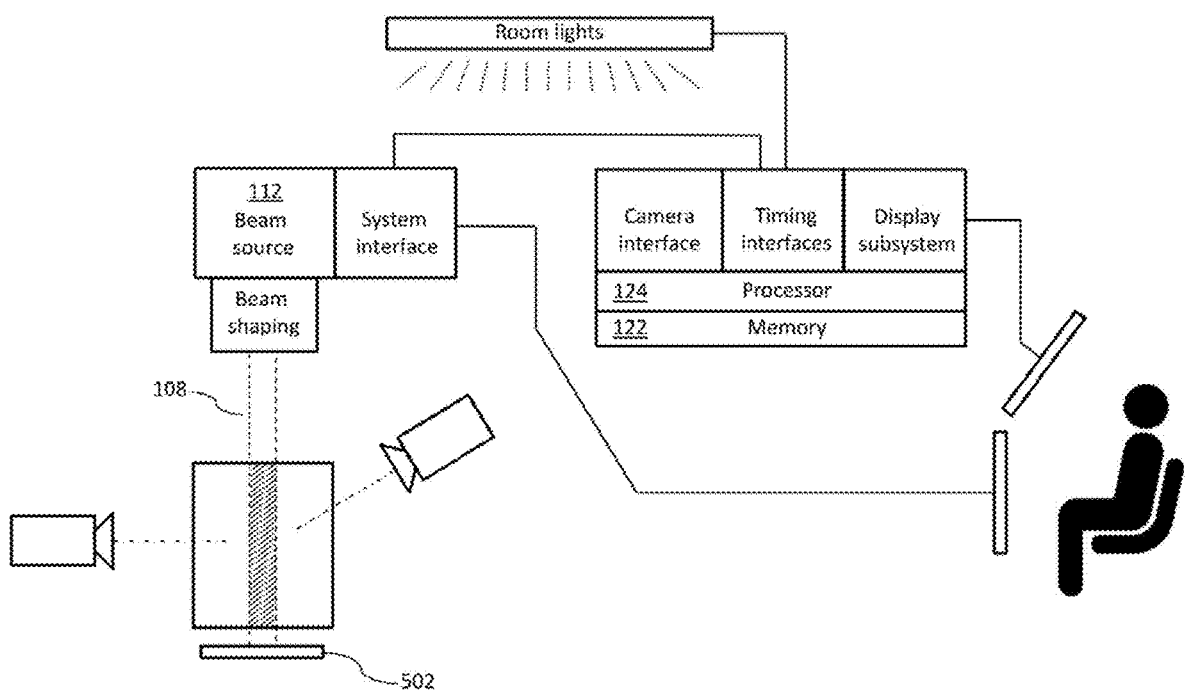
FIG. 5 is a schematic block diagram of an apparatus for coordinated Cherenkov and non-Cherenkov observation high-energy beam profiles in a therapeutic radiation system.

Reference is now made to FIG. 5, which schematically depicts portions of an illustrative system 500 according to certain embodiments. System 500 resembles system 200 of FIG. 2 but with the addition of a non-Cherenkov radiation measurement device 502. In one example, the imaging device 502 is an external portal imaging device (EPID). One type of EPID consists essentially of a converter layer that converts incident radiation into light and a two-dimensional array of electronic sensors capable of sensing the light thus produced. In certain embodiments, the converter layer may consist essentially of some form of metal plate in contact with either an ionization medium or a phosphor screen. Further, in certain embodiments, the detection array may be in a camera trained upon the converter, or in extended solid-state array (active matrix flat panel) parallel and close to the converter. In some EPID technologies, conversion is omitted in favor of direct detection by active matrix flat-panel devices. In essence, an EPID serves as a piece of electronic film whose image may be retrieved, in the form of digital data, at relatively high speed and without the need for development.

Regardless of technological basis, a typical EPID is capable of imaging a rectangular two-dimensional cross-section of the beam 108 (typically orthogonal to the beam 108) at a given distance from the source 112. In one illustrative system 500, data from the EPID may be routed to the memory 122 and processor 124 of the Cherenkov imaging system 120, e.g., via a quantifier integration unit described herein; in certain alternative embodiments, EPID data may be separately processed through a different interface, memory, and processing system (not depicted), such as is already provided in an integral manner with some LINAC or other therapeutic-radiation systems, before being routed to or integrated with the Cherenkov imaging subsystem 120. Provisions for mounting, moving, and communicating with the EPID are for simplicity omitted from FIG. 5, but the nature of such provisions will be familiar to persons versed in the construction of such devices, in light of the disclosure herein.

Certain embodiments employ one or more non-Cherenkov measurement devices, which may employ one or more sensing modalities (e.g., ionization, direct-detection flat panel), to acquire beam information. In one example, the EPID of FIG. 5 acquires lateral beam information, i.e., oneor two-dimensional radiation intensity information in the plane of the non-Cherenkov device, which is orthogonal to the beam 108. In addition to non-Cherenkov dose information, Cherenkov emission information is acquired from one or more viewpoints, e.g., by a moving camera, or a camera fixed relative to a moving irradiation target, or by a multiplicity of cameras. Thus, in certain embodiments, information on delivered dose is obtained from a plurality of viewpoints using at least two distinct sensing modalities, one of which is Cherenkov imaging. In one example, the lateral profile or extent of the beam at the back of the treatment area (i.e., in the position of the EPID 502 depicted in FIG. 5) can be measured and, with assumptions based on lateral beam divergence and penumbra, estimates of the three-dimensional image of beam 108 can be made. This information, combined with axial decay of the signal from lateral Cherenkov imaging, can be used to estimate full four-dimensional dosimetry in a water tank or other phantom.

Advantageously, the system enables measurements to be made in real time, allowing characterization of phantom-delivered complex treatment plans at all points in the treatment. This can be a valuable tool for routine patient plan verification prior to delivery in the patient; verification could be performed on each plan prior to delivery. This is especially important for complex treatment plans, where verification is not only necessary but is reimbursed by some systems of health-care funding (e.g., by Medicare in the US, as "pretreatment simulation").

In addition, in certain embodiments of the system, the EPID or other non-Cherenkov imaging information is combined with Cherenkov imaging acquired during actual patient irradiation. Although Cherenkov light cannot typically be detected from deep within human tissue, surficial Cherenkov light may be imaged as a proxy for skin dose. In effect, Cherenkov light emitted at or just below the skin surface upon beam entry serves as a cross-sectional (through the generally non-planar skin surface) image of the incident beam, conveying information both on intensity profile and overall geometry: this information can be combined with beam profile data transmitted through the medium and detected by EPID or other non-Cherenkov information using a variety of mathematical modeling procedures to produce estimates of internal patient dose geometry, and in certain embodiments, with high temporal resolution, that are more accurate than those achievable from either Cherenkov or non-Cherenkov sensing alone. It is advantageous for patient safety and treatment efficacy to have improved knowledge of internal dosage geometry.

III. Methods of Cherenkov-Based Imaging

We provide methods using a radio-optical triggering unit (RTU). Such methods include, methods of radio-optical triggering comprising:

detection of scattered radiation by a fast response time scintillator (SCI) coupled with a high speed, single photon sensitive, silicon photomultiplier module (SiPM)) upon exposure of a subject to high-energy radiation from a radiation beam source;

conversion and amplification of the scattered radiation into optical photons, generating an analog electrical signal;

processing the analog signal to a digital timing signal, wherein the digital timing signal is synchronized with the radiation beam source; and communication of the digital timing signal to trigger the operation of at least one camera capable of imaging Cherenkov radiation, such that the operation of said camera is triggered to detect Cherenkov radiation for Cherenkov imaging purposes.

Versatile RTU

With reference to FIGS. 11, 12, 13, and 14, a versatile RTU 1000 includes a fast-response radiation detector 1002. In an embodiment, the fast-response radiation detector uses a fast-response scintillator coupled to a fast-response photodetector, in an alternative embodiment the fast-response radiation detector 1002 is a semiconductor radiation detector. The fast-response radiation detector 1002 provides a raw output 1016 synchronized to pulses of the radiation and which may be used as above described to trigger cameras to detect Cherenkov radiation.

Signals from the fast response radiation detector 1002 are not well timed for detecting background images or fluorescent images, in addition there may be shutter delays and risetime delays. In an embodiment, signals from the fast response radiation detector 1002 are detected 1050 and measured 1052 as to time 1030 of occurrence, and width 1032 by pulse timing and measurement circuits 1004, providing this information to processor 1008. Processor 1008, operating under control of machine readable instructions of firmware in memory 1010, determines a radiation pulse rate and radiation pulse width from the time of occurrence of multiple radiation pulses, and predicts 1054 a time 1024 of occurrence for each next radiation pulse, instructing pulse generator circuits 1006 to generate 1056 a synchronized pulse 1028 output 1018 during each next radiation pulse. Processor 1008 also instructs pulse generator circuits 1006 to provide a signal 1022, bearing a pulse 1023 just after an end of the radiation pulse to be used for imaging fluorescent emissions before they decay, and an output 1020 bearing a pulse 1021 late in each pulse-to-pulse interval to trigger capture of background images for background subtraction.

Figure 11:
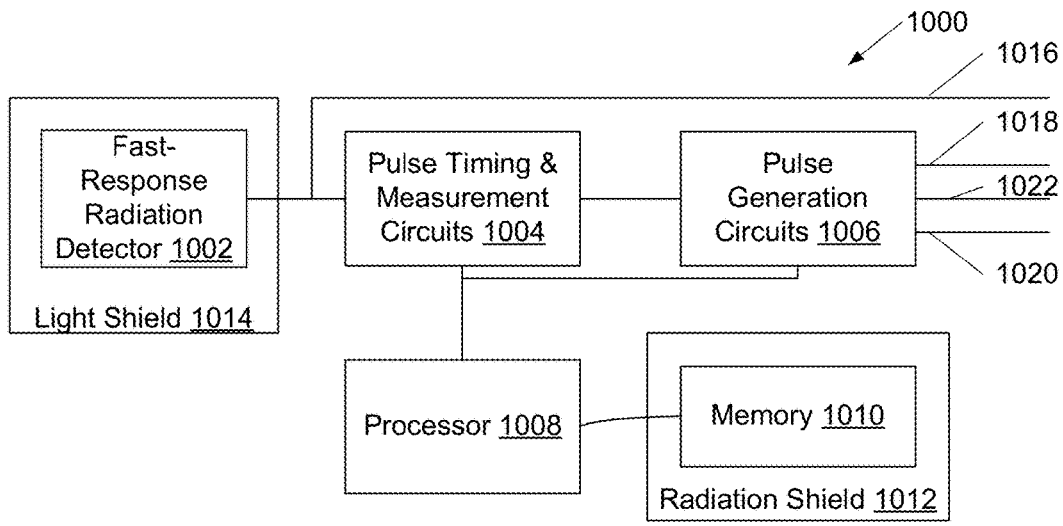
FIG. 11 is a block diagram of a versatile RTU providing raw pulses indicative of detected radiation pulses, synthesized pulses synchronized to detected radiation pulses, synthesized pulses immediately following detected radiation when fluorescent emissions are expected, and synthesized pulses leading expected radiation pulses for background image capture.
Figure 12:
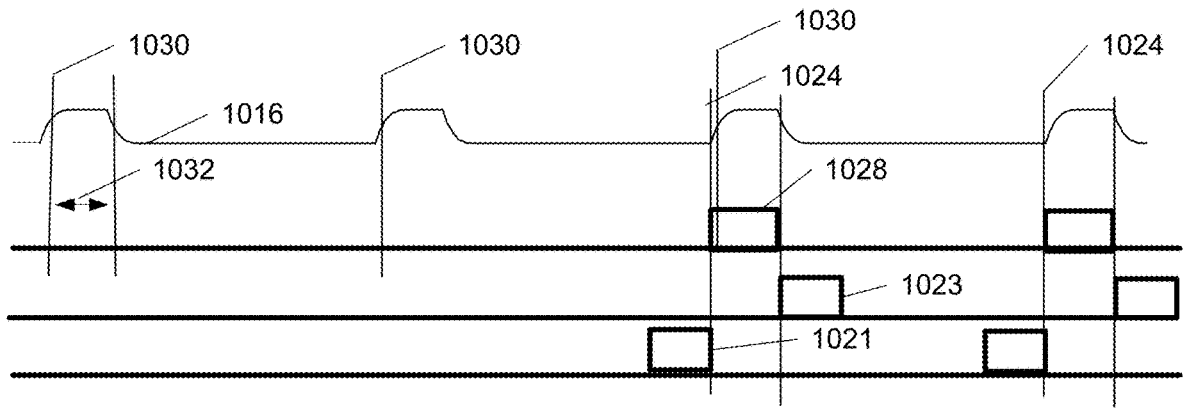
FIG. 12 is a timing diagram of the versatile RTU of FIG. 11.
Figure 13:
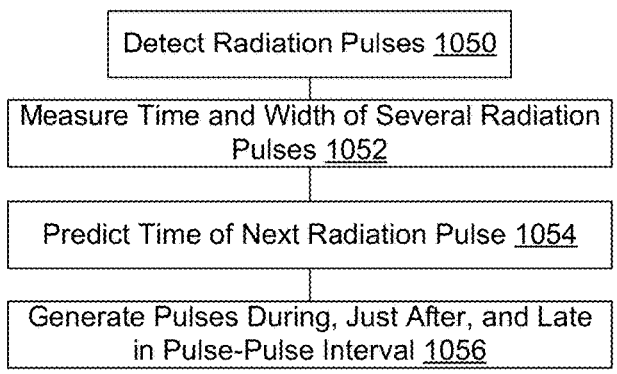
FIG. 13 is a flowchart of operation of the versatile RTU of FIG. 11.
Figure 14:
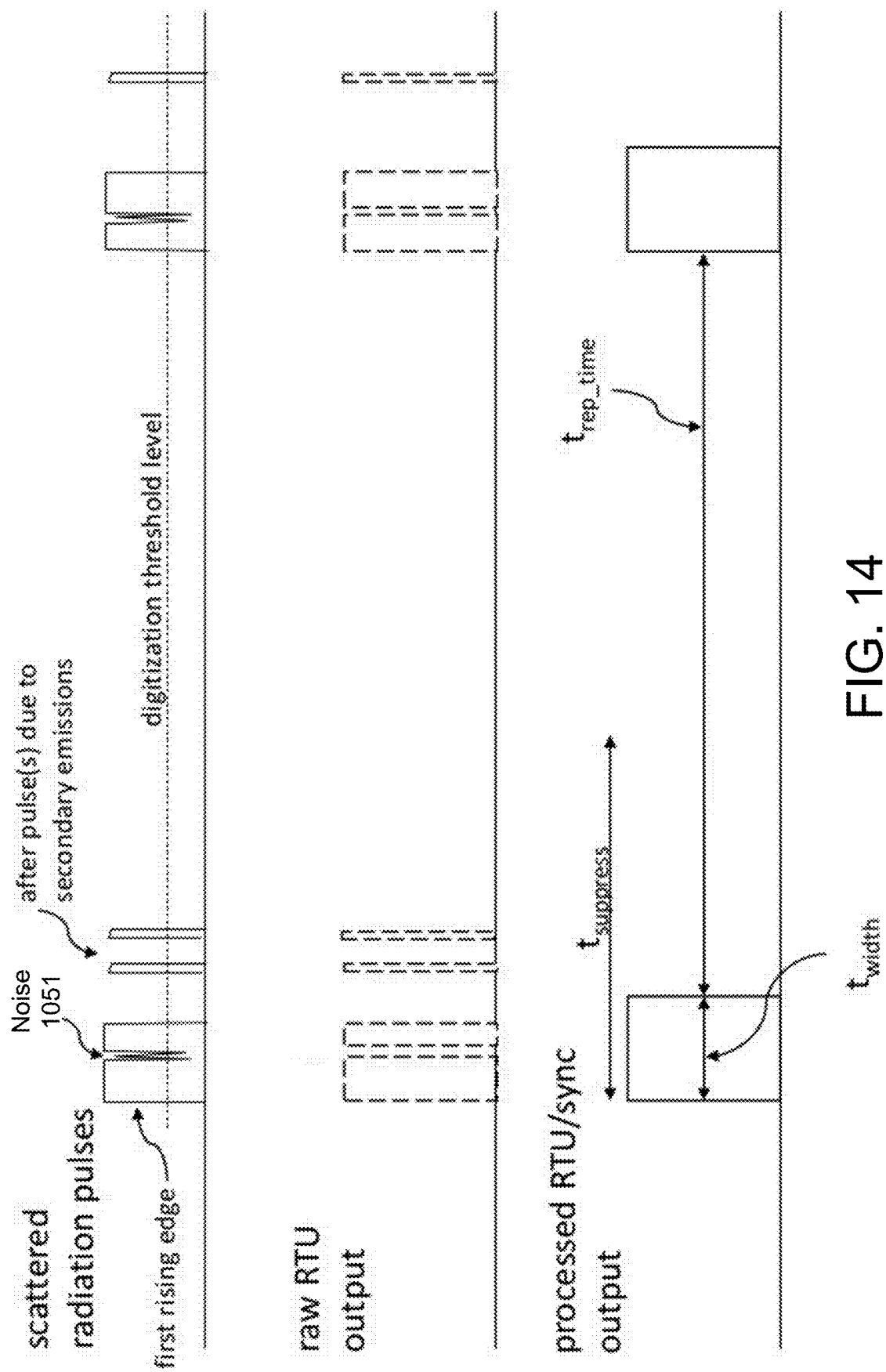
FIG. 14 is a timing diagram of a versatile RTU resembling FIG. 11.

In a particular embodiment of the versatile RTU of FIG. 11, pulse generation circuits 1006 are generate an RTU output pulse of specified duration ($t_{width}$), in sync with primary radiation pulse, and ignoring any momentary dropouts 1051 from noise, and suppress retriggering at within a specified dead time ($t_{suppress}$) to avoid retriggering on stray radiation, such as particles from neutron induced radiation such as may result from high energy proton beams. In a particular embodiment, $t_{suppress}$ and $t_{width}$ are determined dynamically by processor 1008 based upon measurements of width and spacing of pulses observed during treatment by fast-response radiation detector 1002 and measured by pulse timing and measurement circuits 1004. In typical operation the dead time window, ($t_{suppress}$) is less than the repetition period of LINAC pulses such the next arriving radiation pulse is not missed In an alternative embodiment, the versatile RTU of FIGS. 11-14 is built into the camera unit, where the RTU output is processed to output a digital pulse of specified width ($t_{width}$), in sync with the detected rising edge of the primary radiation pulse, and ignores noise pulses happening within a specified dead time window ($t_{suppress}$) to mitigate synchronization issues caused by the spurious pulses output from the RTU.

To prevent interference by room lighting, when the fast response radiation detector 1002 incorporates a scintillator and photodetector, those components are encapsulated in a light shield 1014 configured to exclude light from other sources. Further, to prevent stray or scattered high energy radiation or x-rays from erasing data in electrically-programmable or reprogrammable memory devices, or corrupting data in dynamic RAM memory devices, of memory 1010, memory 1010 is enclosed in radiation shield 1012.

Combinations of Features

The features herein described may be combined in several ways. Among the combinations anticipated include:

A radio-optical triggering unit (RTU) designated A and including high speed radiation detector configured to detect scattered radiation from a radiation beam generated by a pulsed radiation beam source; apparatus configured to generate an analog signal from the photons; apparatus configured to: digitize the analog signal to a digital timing signal synchronized with the pulsed radiation beam source; and communicate the digital timing signal to trigger operation of at least one camera capable of imaging Cherenkov radiation.

An RTU designated AA including the RTU designated A wherein the high-speed radiation detector comprises a scintillator configured to generate photons from scattered radiation from a radiation beam generated by a pulsed radiation beam source; and apparatus configured to generate an analog signal from the photons.

An RTU designated AB including the RTU designated A or AA wherein the high-speed radiation detector comprises a solid-state detector.

An RTU designated AC including the RTU designated A, AA, or AB, wherein the digital time signal is synchronized with the radiation beam source to trigger the at least one camera capable of imaging Cherenkov radiation to image Cherenkov radiation during a pulse of the pulsed radiation source.

An RTU designated AD including the RTU designated A, AA, AB, or AC wherein the at least one camera capable of imaging Cherenkov radiation is triggered to image background images when a pulse of the pulsed radiation source is absent.

An imaging system designated B including an RTU designated A, AA, AB, AC, or AD and further including at least one camera capable of imaging Cherenkov radiation capable of receiving communication from the RTU, and a radiation beam source adapted to provide pulses of high-energy radiation.

A system designated BA including the system designated B, wherein the radiation beam source provides a radiation beam cross-sectionally shaped by a beam-shaping apparatus comprising a multi-leaf collimator.

A system designated BB including the system designated B or BA and including a second RTU and wherein outputs from the first and second RTUs are combined with an AND gate.

A system designated BC including the system designated B, BA, or BC wherein the at least one camera capable of imaging Cherenkov radiation is triggered to capture fluorescent emissions images immediately following but not overlapping a pulse of the pulsed radiation source.

An imaging system designated BD including the system designated B, BA, BB, or BC, and further including a communication tool with one or more processing units that enables the control of a radiation beam source.

What is claimed is:

1. A radio-optical triggering unit (RTU) comprising:
   a high-speed radiation detector configured to provide an analog signal indicative of the radiation detector receiving scattered radiation from a radiation beam generated by a pulsed radiation beam source;
   an apparatus configured to:
     digitize the analog signal to a digital timing signal synchronized with the pulsed radiation beam source without relying on electrical signals from the pulsed radiation beam source; and
     communicate the digital timing signal to trigger operation of at least one camera capable of imaging Cherenkov radiation.

2. The RTU of claim 1 wherein the high-speed radiation detector comprises a scintillator configured to generate photons from scattered radiation from a radiation beam generated by a pulsed radiation beam source; and
   apparatus configured to generate an analog signal from the photons.

3. The RTU of claim 1 wherein the high-speed radiation detector comprises a solid-state detector.

4. The RTU of claim 2, wherein the digital time signal is synchronized with the radiation beam source to trigger the at least one camera capable of imaging Cherenkov radiation to image Cherenkov radiation during a pulse of the pulsed radiation source.

5. An imaging system comprising:
   a radio-optical triggering unit of claim 4,
   at least one camera capable of imaging Cherenkov radiation capable of receiving communication from the RTU, and
   a radiation beam source adapted to provide pulses high-energy radiation.

6. The RTU of claim 4 wherein the at least one camera capable of imaging Cherenkov radiation is triggered to image background images when a pulse of the pulsed radiation source is absent.

7. The system of claim 6, wherein the radiation beam source provides a beam cross-sectionally shaped by beam-shaping apparatus comprising a multi-leaf collimator.

8. The system of claim 5 wherein the at least one camera capable of imaging Cherenkov radiation is triggered by the RTU to capture fluorescent emissions images immediately following but not overlapping a pulse of the pulsed radiation source.

9. The RTU of claim 5, wherein the RTU comprises a scintillator and photodetector encapsulated in a light tight enclosure.

10. An imaging system comprising:
    a radio-optical triggering unit of claim 1, and
    at least one camera capable of imaging Cherenkov radiation capable of receiving communication from the RTU.

11. The system of claim 10, further comprising a communication tool with one or more processing units that enable the control of a radiation beam source.

12. The system of claim 11, further comprising a radiation beam source.

13. The system of claim 12, wherein the radiation beam source is a particle accelerator or other device for providing high-energy radiation.

14. The system of claim 13, wherein the radiation beam source may be cross-sectionally shaped by a beam-shaping apparatus comprising a multi-leaf collimator.

15. The system of claim 13, further comprising one or more additional RTUs, and wherein outputs from at least two RTUs are combined using a logical AND gate.

16. The RTU of claim 3, wherein the digital time signal is synchronized with the radiation beam source to trigger the at least one camera capable of imaging Cherenkov radiation to image Cherenkov radiation during a pulse of the pulsed radiation source.

17. An imaging system comprising:
    a radio-optical triggering unit of claim 2, and at least one camera capable of imaging Cherenkov radiation capable of receiving communication from the RTU.

18. An imaging system comprising:
a radio-optical triggering unit of claim 3,
and
at least one camera capable of imaging Cherenkov radiation capable of receiving communication from the RTU.

19. A system comprising a first radio-optical triggering unit (RTU) comprising:
a high-speed radiation detector configured to generate photons from scattered radiation from a radiation beam generated by a pulsed radiation beam source and provide an analog signal;
an apparatus configured to:
digitize the analog signal to a digital timing signal synchronized with the pulsed radiation beam source;
communicate the digital timing signal to trigger operation of at least one camera capable of imaging Cherenkov radiation;
wherein the high-speed radiation detector comprises a scintillator configured to generate photons from scattered radiation from a radiation beam generated by a pulsed radiation beam source, and apparatus configured to generate an analog signal from the photons;
wherein the digital time signal is synchronized with the radiation beam source to trigger the at least one camera capable of imaging Cherenkov radiation to image Cherenkov radiation during a pulse of the pulsed radiation source;
wherein the at least one camera capable of imaging Cherenkov radiation is triggered to image background images when a pulse of the pulsed radiation source is absent; and
further comprising a second RTU and wherein outputs from the first and second RTUs are combined with an AND gate.

20. A method of triggering unit (RTU) comprising:
a high-speed radiation detector configured to provide an analog signal indicative of the radiation detector receiving scattered radiation from a pulsed radiation beam;
an apparatus configured to:
digitize the analog signal to a digital timing signal synchronized with pulses of the radiation beam independently of signals from a source of the pulsed radiation beam other than the scattered radiation from the pulsed radiation beam; and
communicate the digital timing signal to trigger operation of at least one camera capable of imaging Cherenkov radiation.

\* \* \* \* \*